United States Patent
Singh et al.

(12)

(10) Patent No.: US 10,016,372 B2
(45) Date of Patent: Jul. 10, 2018

(54) TRANSDERMAL DELIVERY SYSTEMS WITH PHARMACOKINETICS BIOEQUIVALENT TO ORAL DELIVERY

(71) Applicant: Corium International, Inc., Menlo Park, CA (US)

(72) Inventors: Parminder Singh, Union City, CA (US); Eun Soo Lee, Redwood City, CA (US); Amit K. Jain, Milpitas, CA (US)

(73) Assignee: Corium International, Inc., Menlo Park, CA (US)

( * ) Notice: Subject to any disclaimer, the term of this patent is extended or adjusted under 35 U.S.C. 154(b) by 0 days.

(21) Appl. No.: 15/660,933

(22) Filed: Jul. 26, 2017

(65) Prior Publication Data

US 2018/0028467 A1 Feb. 1, 2018

Related U.S. Application Data

(60) Provisional application No. 62/504,408, filed on May 10, 2017, provisional application No. 62/504,391, filed on May 10, 2017, provisional application No. 62/457,794, filed on Feb. 10, 2017, provisional application No. 62/423,133, filed on Nov. 16, 2016, provisional application No. 62/367,542, filed on Jul. 27, 2016, provisional application No. 62/367,502, filed on Jul. 27, 2016.

(51) Int. Cl.
| | |
|---|---|
| *A61K 9/70* | (2006.01) |
| *A61K 31/445* | (2006.01) |
| *A61K 9/00* | (2006.01) |
| *A61K 47/32* | (2006.01) |
| *A61K 47/10* | (2017.01) |
| *A61K 47/02* | (2006.01) |
| *A61K 47/12* | (2006.01) |

(52) U.S. Cl.
CPC .......... *A61K 9/7084* (2013.01); *A61K 9/0014* (2013.01); *A61K 31/445* (2013.01); *A61K 47/02* (2013.01); *A61K 47/10* (2013.01); *A61K 47/12* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 3,391,142 A | 7/1968 | Mills et al. | |
| 3,546,141 A | 12/1970 | Washburn et al. | |
| 3,549,016 A | 12/1970 | Rigopulos | |
| 4,122,193 A | 10/1978 | Scherm et al. | |
| 4,273,774 A | 6/1981 | Scherm | |
| 4,781,924 A | 11/1988 | Lee et al. | |
| 4,837,027 A | 6/1989 | Lee et al. | |
| 4,886,812 A | 12/1989 | Griss et al. | |
| 4,895,841 A | 1/1990 | Sugimoto et al. | |
| 5,026,556 A | 6/1991 | Drust et al. | |
| 5,061,703 A | 10/1991 | Bormann et al. | |
| 5,123,900 A | 6/1992 | Wick | |
| 5,252,588 A | 10/1993 | Azuma et al. | |
| 5,424,077 A | 6/1995 | Lajoie | |
| 5,614,560 A | 3/1997 | Lipton | |
| 5,866,585 A | 2/1999 | Fogel | |
| 5,958,919 A | 9/1999 | Olney et al. | |
| 6,004,578 A | 12/1999 | Lee et al. | |
| 6,255,348 B1 | 7/2001 | Elstner | |
| 6,383,471 B1 | 5/2002 | Chen et al. | |
| 6,512,010 B1 | 1/2003 | Gale et al. | |
| 6,521,639 B1 | 2/2003 | Murahashi et al. | |
| 6,746,689 B2 | 6/2004 | Fischer et al. | |
| 6,923,988 B2 | 8/2005 | Patel et al. | |
| 6,929,801 B2 | 8/2005 | Klose et al. | |
| 7,097,853 B1 | 8/2006 | Garbe et al. | |
| 7,176,185 B2 | 2/2007 | Hilfinger et al. | |
| 7,250,394 B2 | 7/2007 | Nedergaard | |

(Continued)

FOREIGN PATENT DOCUMENTS

| | | |
|---|---|---|
| CN | 102048678 A | 5/2011 |
| CN | 105693556 A | 6/2016 |

(Continued)

OTHER PUBLICATIONS

US 9,095,635, 08/2015, Willmann et al. (withdrawn)
Aida et al., "Adhesive patch useful in pharmaceuticals, for delivering drugs, provides single surface of support with adhesive layer, where adhesive layer contains drug in solution stae and crystalline state", Database WPI, AN 2008-F37689 (2013).
Brantseva et al., "Rheological and adhesive properties of PIB-based pressure-sensitive adhesives with montmorilionite-type nanofillers", European Polymer Journal, vol. 76, pp. 228-244 (2016).
Chladek et al., "Steady-state bioequivalence studies of two memantine tablet and oral solution formulations in healthy volunteers", J. Appl. Biomed., vol. 6, pp. 39-45 (2008).
Choi et al., "Effect of fatty acids on the transdermal delivery of donepezil: in vitro and in vivo evaluation", Int. J. Pharm., vol. 422, No. 1-2, pp. 83-90 (2012).

(Continued)

*Primary Examiner* — David J Blanchard
*Assistant Examiner* — Daniel F. Coughlin
(74) *Attorney, Agent, or Firm* — McDermott Will & Emery LLP

(57) ABSTRACT

A method for delivering a therapeutic agent to a subject from a transdermal delivery system is described, where the therapeutic agent (i) has a half-life in the blood when delivered orally of greater than about 48 hours and (ii) is for the treatment of a chronic condition. The transdermal delivery system achieves transdermal delivery of the therapeutic agent at steady state that is bioequivalent to administration of the therapeutic agent orally, wherein bioequivalency is established by (a) a 90% confidence interval of the relative mean Cmax and AUC of the therapeutic agent administered from the transdermal delivery system and via oral delivery between 0.70 and 1.43 or between 0.80 and 1.25, or (b) a 90% confidence interval of the ratios for AUC and Cmax of the therapeutic agent administered from the transdermal delivery system and via oral delivery between 0.70 and 1.43 or between 0.80 and 1.25.

18 Claims, 11 Drawing Sheets

(56) References Cited

U.S. PATENT DOCUMENTS

| | | | |
|---|---|---|---|
| 7,320,802 B2 | 1/2008 | Ryde et al. | |
| 7,335,379 B2 | 2/2008 | Carrara et al. | |
| 7,462,743 B2 | 12/2008 | Merli et al. | |
| 7,670,838 B2 | 3/2010 | Deisseroth et al. | |
| 7,682,628 B2 | 3/2010 | Singh | |
| 7,858,114 B2 | 12/2010 | Ito | |
| 7,888,422 B2 | 2/2011 | Jackson et al. | |
| 8,058,291 B2 | 11/2011 | Went et al. | |
| 8,168,209 B2 | 5/2012 | Went et al. | |
| 8,246,978 B2 | 8/2012 | Kydonieus et al. | |
| 8,252,321 B2 | 8/2012 | Dipierro et al. | |
| 8,283,379 B2 | 10/2012 | Went et al. | |
| 8,362,085 B2 | 1/2013 | Went et al. | |
| 8,512,742 B2 | 8/2013 | Amano et al. | |
| 8,614,274 B2 | 12/2013 | Jackson et al. | |
| 8,673,338 B2 | 3/2014 | Bleier | |
| 8,784,879 B2 | 7/2014 | Singh et al. | |
| 8,815,281 B2 | 8/2014 | Kanios et al. | |
| 8,840,922 B2 | 9/2014 | Kawakami et al. | |
| 8,840,935 B2 | 9/2014 | Haber et al. | |
| 8,874,879 B2 | 10/2014 | Ge et al. | |
| 9,012,511 B2 | 4/2015 | Neville et al. | |
| 9,248,104 B2 | 2/2016 | Valia et al. | |
| 9,622,986 B2 | 4/2017 | Im et al. | |
| 2002/0192243 A1* | 12/2002 | Hsu | A61K 8/0208 424/400 |
| 2003/0170308 A1 | 9/2003 | Cleary et al. | |
| 2004/0022835 A1 | 2/2004 | Pai et al. | |
| 2004/0087658 A1 | 5/2004 | Moebius | |
| 2005/0113458 A1 | 5/2005 | Gupta et al. | |
| 2006/0035888 A1 | 2/2006 | Jonas et al. | |
| 2006/0205822 A1 | 9/2006 | Jonas et al. | |
| 2008/0038328 A1 | 2/2008 | Higo et al. | |
| 2008/0107719 A1 | 5/2008 | Likitlersuang et al. | |
| 2008/0131490 A1 | 6/2008 | Hanatani et al. | |
| 2008/0131491 A1 | 6/2008 | Hanatani et al. | |
| 2009/0081259 A1 | 3/2009 | Jonas et al. | |
| 2009/0124659 A1 | 5/2009 | Moebius | |
| 2009/0156639 A1 | 6/2009 | Trippodi-Murphy et al. | |
| 2009/0175929 A1 | 7/2009 | Terahara et al. | |
| 2010/0178037 A1 | 7/2010 | Chen et al. | |
| 2010/0227852 A1 | 9/2010 | Moebius | |
| 2011/0059141 A1 | 3/2011 | Ito | |
| 2011/0059169 A1 | 3/2011 | Went et al. | |
| 2011/0313372 A1 | 12/2011 | Eifler et al. | |
| 2012/0245537 A1 | 9/2012 | Horstmann et al. | |
| 2013/0053358 A1* | 2/2013 | Aida | A61K 9/7061 514/171 |
| 2014/0052081 A1 | 2/2014 | Yang et al. | |
| 2014/0322284 A1 | 10/2014 | Singh et al. | |
| 2014/0370076 A1 | 12/2014 | Choi et al. | |
| 2015/0098980 A1 | 4/2015 | Pongpeerapat et al. | |
| 2016/0051486 A1 | 2/2016 | Choi et al. | |

FOREIGN PATENT DOCUMENTS

| | | |
|---|---|---|
| EP | 0540623 B1 | 9/1994 |
| EP | 1423100 A1 | 6/2004 |
| EP | 1682109 B1 | 10/2008 |
| EP | 2016941 A1 | 1/2009 |
| EP | 2090310 A1 | 8/2009 |
| EP | 2098233 A1 | 9/2009 |
| EP | 2098235 A1 | 9/2009 |
| EP | 2260839 A2 | 12/2010 |
| EP | 2514415 A1 | 10/2012 |
| EP | 2638906 A1 | 9/2013 |
| WO | WO 1996/040087 A2 | 12/1996 |
| WO | WO 2003/020248 A1 | 3/2003 |
| WO | WO 2005/079779 A1 | 9/2005 |
| WO | WO 2010/051349 A1 | 5/2010 |
| WO | WO 2011/070361 A1 | 6/2011 |
| WO | WO 2011/081628 A1 | 7/2011 |
| WO | WO 2012/097197 A1 | 7/2012 |
| WO | WO 2015/053878 A1 | 4/2015 |
| WO | WO 2016/099198 A1 | 6/2016 |
| WO | WO 2016/209982 A1 | 12/2016 |
| WO | WO 2017/018321 A1 | 2/2017 |
| WO | WO 2017/117554 A1 | 7/2017 |

OTHER PUBLICATIONS

Del Rio-Sancho, "Transdermal absorption of memantin-effect of chemical enhancers, iontophoresis, and role of enhancer lipophilicity", Eur J. Pharm. Biopharm., vol. 82, No. 1, pp. 164-170 (2012).

Fang et al., "Donepezil percutaneous absorption enhancer and back lining layer which includes polyethylene, polyester and ethylene-vinyl acetate copolymer", Database WPI, AN 2013-G75464 (2013).

Forchetti, "Treating patients with moderate to severe Alzheimer's disease: implications of recent pharmacologic studies", Prim. Care Companion J. Clin. Psychiatry., vol. 7, No. 4, pp. 155-161 (2005).

Fornasari et al., "Synthesis and antioxidant properties of novel memantine derivatives", Cent. Nerv. Syst. Agents Med. Chem., vol. 17, No. 2, pp. 123-128 (2017).

International Search Report from International Application No. PCT/US2016/038792 dated Sep. 27, 2016.

Kato, Patch used for treating Alzheimer-type dementia, comprises support portion, adhesive layer, donepezil and/or its hydrochloride, and additive chosen from isostearic acid, 2-cetyl ethylhexanoate, and hexadecyl isostearate, Database WPI, AN 2014-C88308 (2014).

Pastore et al., "Transdermal patches: history, development and pharmacology", Br. J. Pharmacol., vol. 172, No. 9, pp. 2179-2209 (2015).

Ravi and Gupta, "The treatment of alzheimers disease by using donopezil loaded transdermal patch", J. Chem. Pharm. Res., vol. 7, No. 3, pp. 806-813 (2015).

Schulz et al., "Therapeutic and toxic blood concentrations of nearly 1,000 drugs and other xenobiotics", Crit. Care, vol. 16, No. R136, 4 pgs. (2012).

Sozio et al., "Transdermal donepezil on the treatment of Alzheimer's disease", Neuropsychiatr. Dis. Treat., vol. 8, pp. 361-368 (2012).

Tiseo et al., "Pharmacokinetic and pharmacodynamic profile of donepezil HCl following evening administration", Br. J. Pharmacol. vol. 46, Suppl. 1, pp. 13-18 (1998).

Ashall, "Tobacco Facts #4: Smokers are freebasing nicotine!—The Great Tobacco Plague", Dr Frank Ashalls Blog, Retreived from the Internet: https://biochemdr1.wordpress.com/2013/11/30/tobacco-fact-4-somkers-are-freebasing-nicotine/, 7 pages (Nov. 30, 2013).

International Search Report from International Patent Application No. PCT/US2017/044047 dated Nov. 3, 2017.

Partial International Search Report from International Patent Application No. PCT/US2017/044048 dated Nov. 3, 2017.

International Search Report from International Patent Application No. PCT/US2017/044049 dated Nov. 7, 2017.

International Search Report from International Patent Application No. PCT/US2017/044050 dated Nov. 6, 2017.

International Search Report from International Patent Application No. PCT/US2017/044051 dated Nov. 2, 2017.

* cited by examiner

TRANSDERMAL DELIVERY SYSTEMS WITH PHARMACOKINETICS BIOEQUIVALENT TO ORAL DELIVERY

CROSS-REFERENCE TO RELATED APPLICATIONS

This application claims the benefit of U.S. Provisional Application No. 62/504,408, filed May 10, 2017; U.S. Provisional Application No. 62/504,391, filed May 10, 2017; U.S. Provisional Application No. 62/457,794, filed Feb. 10, 2017; U.S. Provisional Application No. 62/423,133, filed Nov. 16, 2016; U.S. Provisional Application No. 62/367,542, filed Jul. 27, 2016; and U.S. Provisional Application No. 62/367,502, filed Jul. 27, 2016, each incorporated herein by reference in its entirety.

TECHNICAL FIELD

The subject matter described herein relates to transdermal delivery of a therapeutic agent from a system designed to provide pharmacokinetics bioequivalent to oral delivery of a similar dose of the therapeutic agent.

BACKGROUND

Transdermal delivery of a therapeutically active agent through the skin provides a means for a sustained, constant plasma level of the agent. It differs from conventional therapy via oral administration in that blood levels remain constant throughout the period during which the transdermal system is on the skin, providing a blood concentration of drug without the peaks and troughs of drug concentration seen in oral delivery. Transdermal delivery is utilized for drugs with a short half-life and/or when there is a significant first-pass effect of the liver that can prematurely metabolizes the drug than long half drugs.

Oral administration of drugs with a long elimination half-life can achieve a relatively constant blood level of drugs with the minimal peaks and valleys within the therapeutic range at the steady state for long half-life drugs. Oral administration of a long half-life drug (not less than 48 hours) brings about accumulation of the drug in the blood over time until it reaches the steady state blood level in the therapeutic range.

It would be desirable to take advantage of the long half-lives of drugs in designing a transdermal delivery system which is therapeutically equivalent to the oral dosage route with respect to the pharmacokinetic parameters of area under the curve (AUC) and maximum blood concentration (Cmax). The achievement of bioequivalence can reduce extensive non-clinical and clinical test costs.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method for delivering a therapeutic agent to a subject is provided. The method comprises providing a transdermal delivery system comprised of a therapeutic agent and a reservoir comprising the therapeutic agent, wherein the therapeutic agent (i) has a half-life in the blood when delivered orally of greater than about 48 hours and (ii) is for the treatment of a chronic condition, and administering or instructing to administer the transdermal delivery system to the skin of a subject. The administering achieves transdermal delivery of the therapeutic agent that is bioequivalent to administration of the therapeutic agent orally, wherein bioequivalency is established by (a) a 90% confidence interval of the relative mean Cmax and AUC of the therapeutic agent administered from the transdermal delivery system and via oral delivery between 0.70 and 1.43 or between 0.80 and 1.25, or (b) a 90% confidence interval of the geometric mean ratios for AUC and Cmax of the therapeutic agent administered from the transdermal delivery system and via oral delivery between 0.70 and 1.43 or between 0.80 and 1.25.

In one embodiment, the therapeutic agent is a poorly water soluble agent.

In one embodiment, bioequivalency is established in healthy subjects.

In one embodiment, bioequivalency is established in a fasting condition. In one embodiment, bioequivalency is established in a fed or non-fasting condition. In one embodiment, the bioequivalency is evaluated when one or both of transdermal administering and orally administering is at steady state.

In another embodiment, bioequivalency is established using the same dose of therapeutic agent given orally and transdermally. In another embodiment, the dose of therapeutic agent given transdermally is within about 5%, 10%, or 15% of the dose given orally.

In another embodiment, the therapeutic agent is donepezil base, a donepezil salt, memantine base or a memantine salt. In one specific embodiment, the therapeutic agent is donepezil base or a donepezil salt. In another specific embodiment, the therapeutic agent is memantine base or a memantine salt. In another embodiment, the therapeutic agent is fingolimod base or a fingolimod salt.

In yet another embodiment, the chronic condition is Alzheimer's disease. In yet another embodiment, the chronic condition is multiple sclerosis, including relapsing forms of multiple sclerosis.

In still another embodiment, the administering or instructing to administer comprises administering or instructing to administer once weekly. In still another embodiment, the administering or instructing to administer comprises administering or instructing to administer once daily, twice weekly, or thrice weekly.

In one embodiment, the therapeutic agent is donepezil base or a donepezil salt, and wherein the transdermal delivery system comprises a dose of donepezil base or a donepezil salt to provide between 5-10 mg/24 hours. In one embodiment, the therapeutic agent is donepezil base or a donepezil salt, and wherein the transdermal delivery system comprises a dose of donepezil base or a donepezil salt to provide between 1-25 mg/24 hours.

In another embodiment, the transdermal delivery system comprises a drug reservoir and a contact adhesive, wherein the drug reservoir comprises a hydrophilic solvent, and the drug reservoir and/or the contact adhesive comprises one of (i) permeation enhancer, (ii) triethyl citrate, and (iii) a polyvinylpyrrolidone.

In yet another embodiment, the transdermal delivery system comprises a drug reservoir and a contact adhesive, wherein the drug reservoir comprises glycerol and the drug reservoir and/or the contact adhesive comprises one of (i) lauryl lactate, (ii) triethyl citrate, and (iii) glycerol. octyldodecanol. In one embodiment, the contact adhesive excludes the hydrophilic solvent present in the drug reservoir. In one embodiment, the contact adhesive excludes glycerol.

In still another embodiment, the transdermal delivery system comprises a drug reservoir comprises two of (i) lauryl lactate, (ii) triethyl citrate, and (iii) glycerol. In still another embodiment, the transdermal delivery system comprises a drug reservoir comprises two of (i) lauryl lactate, (ii) triethyl citrate, (iii) glycerol, and (iv) sorbitan monolaurate.

In one embodiment, the drug reservoir comprises donepezil hydrochloride and sodium bicarbonate. In one embodiment, the drug reservoir is manufactured from a formulation that comprises donepezil hydrochloride and sodium bicarbonate. In another embodiment, the drug reservoir comprises donepezil base generated in situ by a reaction of donepezil hydrochloride and sodium bicarbonate.

In one embodiment, the transdermal delivery system comprises a drug (therapeutic agent) reservoir, wherein the drug reservoir is manufactured from a formulation comprising a salt form of the therapeutic agent and an alkaline salt, and the drug reservoir comprises in equilibrium, the salt form of the therapeutic agent, the alkaline salt, and a base form of the therapeutic agent. In another embodiment, the transdermal delivery system comprises a drug (therapeutic agent) reservoir which comprises the salt form of the therapeutic agent, the alkaline salt, and a base form of the therapeutic agent. In one embodiment, the therapeutic agent is donepezil; in another embodiment the therapeutic agent is memantine; and in another embodiment the therapeutic agent is fingolimod.

In one embodiment, the transdermal delivery system comprises a drug reservoir comprising or consisting essentially of (a) donepezil base generated in situ by reaction of between about 5-30 wt % or 5-25 wt % or 10-30 wt % donepezil salt and between about 0.5-10 wt % alkaline salt and about 25-60 wt %, 25-65 wt % or 30-65 wt % acrylate copolymer. In one embodiment, the donepezil salt is donepezil hydrochloride (donepezil HCl); the alkaline salt is sodium bicarbonate or potassium bicarbonate.

In another embodiment, the transdermal delivery system comprises a drug reservoir and a contact adhesive, wherein the drug reservoir comprises (i) an acrylate polymer, (ii) a dissolving agent, (iii) a carrier, (iv) an optional disintegrant, and (v) memantine base generated in situ by reaction of a salt of memantine with an alkaline salt. In embodiments, the acrylate polymer comprises vinyl acetate and at least one acrylate selected from the group consisting of 2-ethylhexyl-acrylate, hydroxyethyl acrylate and glycidyl acrylate. Additionally or alternately in embodiments, the dissolving agent is a higher alcohol selected from the group consisting of lauryl alcohol, isostearyl alcohol, octyldodecanol, and oleyl alcohol. Additionally or alternately in embodiments, the carrier is a hydrophilic solvent, which may, in some embodiments, be selected from the group consisting of glycerol (glycerin), propylene glycol, liquid polyethylene glycol, acetonitrile, 1-propanol, N,N-dimethylformamide and dimethyl sulfoxide. Additionally or alternately in embodiments, the disintegrant is selected from the group consisting of polyvinylpyrrolidone (PVP) or polyvinyl alcohol (PVA), or cross-linked derivative thereof. In one embodiment, the disintegrant is cross-linked polyvinylpyrrolidone (PVP-CLM). Additionally or alternately in embodiments, the memantine salt is a halide salt of memantine. In embodiments, the memantine salt is memantine hydrochloride (memantine HCl). Additionally or alternately under embodiments, the alkaline salt is selected from the group consisting of sodium acetate, sodium borate, sodium metaborate, sodium carbonate, sodium bicarbonate, potassium carbonate, potassium bicarbonate, potassium citrate, potassium acetate, sodium phosphate, potassium phosphate, disodium hydrogen phosphate, sodium oxylate, sodium succinate, sodium citrate, and sodium salicylate. In one embodiment, the alkaline salt is potassium bicarbonate or sodium bicarbonate. The drug reservoir may optionally contain an additional agent selected from sorbitan monolaurate and lauryl lactate.

In yet another embodiment, the transdermal delivery system comprises a drug reservoir and a contact adhesive, wherein the contact adhesive comprises (1) a dissolving agent and (2) a biocompatible polymer, optionally together with (3) a matrix modifier and further optionally (4) dispersive silica. In embodiments, the dissolving agent is a higher alcohol selected from the group consisting of lauryl alcohol, isostearyl alcohol, octyldodecanol, and oleyl alcohol. In one embodiment, the higher alcohol is octyldodecanol. Alternately or additionally, the biocompatible polymer is selected from the group consisting of polyisobutylene (PIB), a silicone polymer, acrylate copolymers, butyl rubber, polybutylene, styrene-iosprene-styrene block copolymers, styrene-butadiene-styrene block copolymers, ethylene-vinyl acetate (EVA), a mixture thereof or a copolymer thereof. In one embodiment, the biocompatible polymer comprises polyisobutylene. Alternately or additionally, the matrix modifier is selected from the group consisting of cross-linked polyvinylpyrrolidone (PVP), soluble PVP, cellulose derivatives, polyacrylamide, polyacrylic acid and clay. In one embodiment, the matrix modifier is cross-linked polyvinylpyrrolidone (PVP-CLM). Still alternately or additionally, the dispersive silica used in the delivery system is pharmaceutical grade amorphous anhydrous colloidal silicon dioxide. In one embodiment, the contact adhesive does not comprise the active ingredient. In one embodiment, the contact adhesive does not comprise the hydrophilic solvent present in the drug reservoir. In one embodiment, the contact adhesive does not comprise glycerol.

In one embodiment, the systems comprise a drug reservoir comprising or consisting essentially of (a) memantine base generated in situ by reaction of between about 10-30 wt % memantine salt and between about 5-15 wt % alkaline salt; (b) about 5-15 wt % dissolving agent; (c) about 5-15 wt % carrier; (d) about 10-30 wt % disintegrant; and (e) about 20-50 wt % acrylate polymer. In one embodiment, the memantine salt is memantine hydrochloride (memantine HCl); the alkaline salt is sodium bicarbonate or potassium bicarbonate; the dissolving agent is a higher alcohol selected from the group consisting of lauryl alcohol, isostearyl alcohol, octyldodecanol, and oleyl alcohol; the carrier is glycerol; the disintegrant is crosslinked polyvinylpyrrolidone (PVP-CLM); the acrylate polymer comprises vinyl acetate and at least one acrylate selected from the group consisting of 2-ethylhexyl-acrylate, hydroxyethyl acrylate and glycidyl acrylate.

In another embodiment, the systems comprise a drug reservoir comprising or consisting essentially of (a) memantine base generated in situ by reaction of between about 22-27 wt % memantine salt and between about 7-12 wt % alkaline salt; (b) about 8-12 wt % dissolving agent; (c) about 8-12 wt % carrier; (d) about 13-17 wt % disintegrant; and (e) about 28-35 wt % acrylate polymer. In embodiments, the memantine salt is memantine hydrochloride (memantine HCl); the alkaline salt is sodium bicarbonate or potassium bicarbonate; the dissolving agent is a higher alcohol selected from the group consisting of lauryl alcohol, isostearyl alcohol, octyldodecanol, and oleyl alcohol; the carrier is glycerol; the disintegrant is crosslinked polyvinylpyrrolidone (PVP-CLM); the acrylate polymer comprises vinyl acetate and at least one acrylate selected from the group consisting of 2-ethylhexyl-acrylate, hydroxyethyl acrylate and glycidyl acrylate.

In another embodiment, the systems comprise a drug reservoir comprising or consisting essentially of (a) fingolimod base generated in situ by reaction of fingolimod salt an alkaline salt; (b) a dissolving agent or permeation enhancer; (c) a carrier (hydrophilic solvent); (d) an optional disintegrant; and (e) an acrylate copolymer. In embodiments, the fingolimod salt is fingolimod hydrochloride (fingolimod HCl); the alkaline salt is sodium bicarbonate or potassium bicarbonate; the dissolving agent is lauryl lactate or a higher alcohol selected from the group consisting of lauryl alcohol, isostearyl alcohol, octyldodecanol, and oleyl alcohol; the carrier is glycerol; the hydrophilic solvent carrier is glycerol; the disintegrant is crosslinked polyvinylpyrrolidone (PVP-CLM); and the acrylate copolymer comprises vinyl acetate and at least one acrylate selected from the group consisting of 2-ethylhexyl-acrylate, hydroxyethyl acrylate and glycidyl acrylate.

In another embodiment, systems comprising (a) one or more of the aforementioned drug reservoirs; (b) a rate controlling membrane or a non-woven layer; and (c) a contact adhesive; and (d) optionally a permeation enhancer included in one or both of the drug reservoir and/or the contact adhesive are described. In embodiments, the rate controlling membrane is a microporous polypropylene membrane.

In another embodiment, systems comprising (a) one or more of the aforementioned drug reservoirs; (b) a rate controlling membrane or a non-woven layer; and (c) a contact adhesive comprising a higher alcohol and a biocompatible polymer, optionally together with a matrix modifier and further optionally dispersive silica are provided. In embodiments, the contact adhesive comprises the higher alcohol, the biocompatible polymer and the matrix modifier. In other embodiments, the contact adhesive comprises the higher alcohol, the biocompatible polymer and the dispersive silica.

In a related embodiment, systems comprising (a) one or more of the aforementioned drug reservoirs; (b) a rate controlling membrane or a non-woven layer; and (c) a contact adhesive comprising a higher alcohol selected from the group consisting of lauryl alcohol, isostearyl alcohol, octyldodecanol, and oleyl alcohol and a biocompatible polymer selected from polyisobutylene (PIB), silicone polymers, acrylate copolymers, butyl rubber, polybutylene, styrene-iosprene-styrene block copolymers, styrene-butadiene-styrene block copolymers, ethylene-vinyl acetate (EVA), or a mixture thereof or a copolymer thereof, optionally together with a matrix modifier selected from the group consisting of cross-linked polyvinylpyrrolidone (PVP), soluble PVP, cellulose derivatives, polyacrylamide, polyacrylic acid and clay and further optionally high purity amorphous anhydrous colloidal silicon dioxide are provided.

In one particular embodiment, systems comprising (a) one or more of the aforementioned drug reservoirs; (b) a rate controlling membrane or a non-woven layer; and (c) a contact adhesive comprising about 5-15 wt % of a higher alcohol and about 50-95 wt % of a biocompatible polymer, optionally together with about 10-30 wt % of a matrix modifier and further optionally about 4-12 wt % of dispersive silica are provided. In embodiments, the contact adhesive comprises a higher alcohol which is octyldodecanol, a biocompatible polymer comprising polyisobutylene, and optionally a matrix modifier comprising cross-linked polyvinylpyrrolidone (PVP) and further optionally dispersive silica comprising high purity amorphous anhydrous colloidal silicon dioxide.

In another particular embodiment, systems comprising (a) one or more of the aforementioned drug reservoirs; (b) a rate controlling membrane or a non-woven layer; and (c) contact adhesive comprising about 8-12 wt % of a higher alcohol and about 65-90 wt % of a biocompatible polymer, optionally together with about 15-25 wt % of a matrix modifier and further optionally about 5-10 wt % of dispersive silica are provided. In embodiments, the adhesion matrix comprises a higher alcohol which is octyldodecanol, a biocompatible polymer comprising polyisobutylene, and optionally a matrix modifier comprising cross-linked polyvinylpyrrolidone (PVP) and further optionally dispersive silica comprising high purity amorphous anhydrous colloidal silicon dioxide.

In embodiments, kits comprising, in one or more packages, (a) one or more of the aforementioned drug reservoirs; (b) a rate controlling membrane or a non-woven layer; and (c) a contact adhesive, optionally together with instructions for assembling components (a)-(c) into a delivery system, and additionally or optionally together with instructions for administering the delivery system to a subject in need thereof are provided.

In another embodiment, the therapeutic agent is memantine base or a memantine salt, and wherein the transdermal delivery system comprises a dose of memantine base or memantine salt to provide between 7-28 mg/24 hours.

In yet another embodiment, the transdermal delivery system comprises a drug reservoir comprising one of ethyl acetate and levulinic acid.

In still another embodiment, the therapeutic agent is memantine base.

Also contemplated is a method for treating Alzheimer's disease, comprising applying to the skin of a subject a transdermal delivery system as described herein.

Also contemplated is a method for treating relapsing-remitting multiple sclerosis, comprising applying to the skin of a subject a transdermal delivery system as described herein and which comprises fingolimod (base or salt).

In another embodiment, the therapeutic agent is fingolimod base or a fingolimod salt, and wherein the transdermal delivery system comprises a dose of fingolimod base or fingolimod salt to provide between 0.05-2 mg/24 hours.

In another aspect, a method for evaluating a transdermal system is provided, where the method comprises administering or instructing to administer a transdermal delivery system to a subject, the transdermal delivery system comprised of a therapeutic agent and a reservoir comprising the therapeutic agent, wherein the therapeutic agent (i) has a half-life in the blood when delivered orally of greater than about 48 hours and (ii) is for the treatment of a chronic condition, and administering or instructing to administer to a subject via oral administration the therapeutic agent. The administering achieves transdermal delivery of the therapeutic agent that is bioequivalent to administration of the therapeutic agent orally, wherein bioequivalency is established by (a) a 90% confidence interval of the relative mean $C_{max}$ and AUC of the therapeutic agent administered from the transdermal delivery system and via oral delivery are between 0.70 and 1.43 or are between 0.80 and 1.25, or (b) a 90% confidence interval of the geometric mean ratios for AUC and $C_{max}$ of the therapeutic agent administered from the transdermal delivery system and via oral delivery are between 0.70 and 1.43 or are between 0.80 and 1.25.

In one embodiment, the transdermal delivery system administers a dose of x mg/day to the subject, and wherein the subject administered via oral administration the therapeutic agent receives a dose within 20% of the x mg/day. In one embodiment, x is between 1-50, 1-30, 0.5-25, 1-25, 2-30, 2-25 and 1-25.

In another embodiment, the transdermal delivery system administers a dose of x mg/day to the subject, and wherein the subject administered the therapeutic agent via oral administration receives x mg/day. In one embodiment, x is between 1-50, 1-30, 0.5-25, 1-25, 2-30, 2-25 and 1-25.

In still another embodiment, the subject administered the transdermal delivery system and the subject administered the therapeutic agent via oral administration are the same.

In yet another embodiment, the subject administered the transdermal delivery system and the subject administered the therapeutic agent via oral administration are different.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1A:
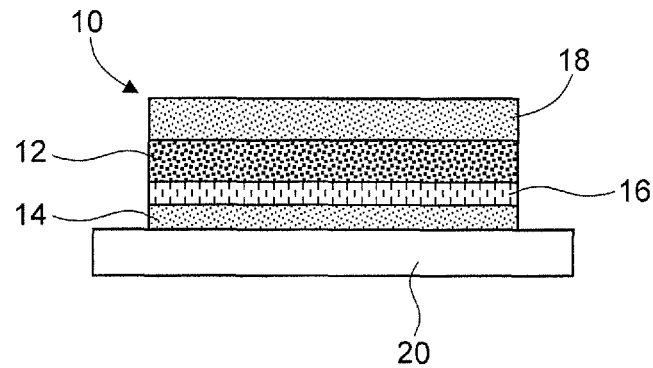
FIGS. 1A-1C are illustrations of transdermal delivery systems according to several embodiments.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "drug" or "active agent" or "therapeutically active agent" are used interchangeably.

By "half-life" is meant the time for one-half of an administered drug to be eliminated through biological processes, e.g. metabolism, excretion, etc.

As used herein, the phrase "therapeutically effective amount" shall mean that drug dosage that provides the specific pharmacological response for which the drug is administered in a significant number of subjects in need of such treatment. It is emphasized that a therapeutically effective amount of a drug that is administered to a particular subject in a particular instance will not always be effective in treating the conditions/diseases described herein, even though such dosage is deemed to be a therapeutically effective amount by those of skill in the art.

The terms "treatment," "therapy," "therapeutic" and the like, as used herein, encompass any course of medical intervention aimed at a pathologic condition, and includes not only permanent cure of a disease, but prevention of disease, control or even steps taken to mitigate a disease or disease symptoms.

The compositions of the present disclosure can comprise, consist essentially of, or consist of, the components disclosed.

All percentages, parts and ratios are based upon the total weight of the topical compositions and all measurements made are at about 25° C., unless otherwise specified.

The phrase "pharmaceutically acceptable" is employed herein to refer to those compounds, salts, compositions, dosage forms, etc., which are, within the scope of sound medical judgment, suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

The term "treating" is used herein, for instance, in reference to methods of treating a disorder, such as Alzheimer's disease, and generally includes the administration of a compound or composition which reduces the frequency of, or delays the onset of, symptoms of a medical condition (e.g., Alzheimer's disease) in a subject relative to a subject not receiving the compound or composition. This can include reversing, reducing, or arresting the symptoms, clinical signs, and underlying pathology of a condition in a manner to improve or stabilize a subject's condition (e.g., regression of mental facilities).

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

II. Method of Treatment

A method for delivering a therapeutic agent transdermally to a subject is provided. In embodiments, the method comprises treatment of one or more central nervous system (CNS) disorders using delivery systems described herein. Examples of CNS disorders include, but are not limited to, dementia (e.g., Alzheimer's disease, Parkinson's disease, Picks disease, fronto-temporal dementia, vascular dementia, normal pressure hydrocephalus, Huntington's disease (HD), and mild cognitive impairment (MCI)), neuro-related conditions, dementia-related conditions, such as epilepsy, seizure disorders, acute pain, chronic pain, chronic neuropathic pain may be treated using the systems and methods described herein. Epileptic conditions include complex partial, simple partial, partials with secondary generalization, generalized—including absence, grand mal (tonic clonic), tonic, atonic, myoclonic, neonatal, and infantile spasms. Additional specific epilepsy syndromes are juvenile myoclonic epilepsy, Lennox-Gastaut, mesial temporal lobe epilepsy, nocturnal frontal lobe epilepsy, progressive epilepsy with mental retardation, and progressive myoclonic epilepsy. The systems and methods described herein are also useful for the treatment and prevention of pain caused by disorders including cerebrovascular disease, motor neuron diseases (e.g. amyotrophic lateral sclerosis (ALS), Spinal motor atrophies, Tay-Sach's, Sandoff disease, familial spastic paraplegia), neurodegenerative diseases (e.g., familial Alzheimer's disease, prion-related diseases, cerebellar ataxia, Friedrich's ataxia, SCA, Wilson's disease, retinitis pigmentosa (RP), ALS, Adrenoleukodystrophy, Menke's Sx, cerebral autosomal dominant arteriopathy with subcortical infarcts (CADASIL); spinal muscular atrophy, familial ALS, muscular dystrophies, Charcot Marie Tooth diseases, neurofibromatosis, von-Hippel Lindau, Fragile X, spastic paraplesia, psychiatric disorders (e.g., panic syndrome, general anxiety disorder, phobic syndromes of all types, mania, manic depressive illness, hypomania, unipolar depression, depression, stress disorders, posttraumatic stress disorder (PTSD), somatoform disorders, personality disorders, psychosis, and schizophrenia), and drug dependence (e.g., alcohol, psychostimulants (e.g., crack, cocaine, speed, meth), opioids, and nicotine), Tuberous sclerosis, and Wardenburg syndrome), strokes (e.g., thrombotic, embolic, thromboembolic, hemmorhagic, venoconstrictive, and venous), movement disorders (e.g., Parkinson's disorder (PD), dystonias, benign essential tremor, tardive dystonia, tardive dyskinesia, and Tourette's syndrome), ataxic syndromes, disorders of the sympathetic nervous system (e.g., Shy Drager, Olivopontoicerebellar degeneration, striatonigral degeneration, Parkinson's disease (PD), Huntington's disease (HD), Gullian Barre, causalgia, complex regional pain syndrome types I and II, diabetic neuropathy, and alcoholic neuropathy), Cranial nerve disorders (e.g., Trigeminal neuropathy, trigeminal neuralgia, Menier's syndrome, glossopharangela neuralgia, dysphagia, dysphonia, and cranial nerve palsies), myelopethies, traumatic brain and spinal cord injury, radiation brain injury, multiple sclerosis, Post-meningitis syndrome, prion diseases, myelities, radiculitis, neuropathies (e.g., Guillian-Barre, diabetes associated with dysproteinemias, transthyretin-induced neuropathies, neuropathy associated with HIV, neuropathy associated with Lyme disease, neuropathy associated with herpes zoster, carpal tunnel syndrome, tarsal tunnel syndrome, amyloid-induced neuropathies, leprous neuropathy, Bell's palsy, compression neuropathies, sarcoidosis-induced neuropathy, polyneuritis cranialis, heavy metal induced neuropathy, transition metal-induced neuropathy, drug-induced neuropathy), axonic brain damage, encephalopathies, and chronic fatigue syndrome. The systems and methods described herein are also useful for the treatment multiple sclerosis, in particular relapsing-remitting multiple sclerosis, and prevention of relapses in multiple sclerosis and/or in relapsing-remitting multiple sclerosis. All of the above disorders may be treated with the systems and methods described herein.

The terms "treatment," "therapy," "therapeutic" and the like, as used herein, encompass any course of medical intervention aimed at a pathologic condition, and includes not only permanent cure of a disease, but prevention of disease, control or even steps taken to mitigate a disease or disease symptoms. For instance, in reference to methods of treating a disorder, such as Alzheimer's disease, the embodiment, generally includes the administration of an active agent which reduces the frequency of, or delays the onset of, symptoms of the medical condition in a subject relative to a subject not receiving the active agent. This can include reversing, reducing, or arresting the symptoms, clinical signs, and underlying pathology of a condition in a manner to improve or stabilize a subject's condition (e.g., regression of mental facilities).

In one embodiment, the therapeutic embodiments are carried out by contacting a tissue of a subject, e.g., skin tissue, with the transdermal delivery systems provided herein.

In another embodiment, the therapeutic embodiments are carried out by transdermally administering the active agent to a subject, e.g., a patient suffering from a CNS disorder such as Alzheimer's disease and/or dementia. The term "administering" means applying as a remedy, such as by the placement of an active agent in a manner in which such drug would be received, e.g., transdermally, and be effective in carrying out its intended purpose.

A "subject" or "patient" in whom administration of the therapeutic agent is an effective therapeutic regimen for a disease or disorder is preferably a human, but can be any animal, including a laboratory animal in the context of a trial or screening or activity experiment. Thus, as can be readily appreciated by one of ordinary skill in the art, the methods and systems as provided herein are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., e.g., for veterinary medical use.

Treatment of a subject with the systems may be monitored using methods known in the art. See, e.g., Forchetti et al., "Treating Patients with Moderate to Severe Alzheimer's Disease: Implications of Recent Pharmacologic Studies." *Prim Care Companion J Clin Psychiatry,* 7(4): 155-161, 2005 (PMID: 16163398). The efficacy of treatment using the system is preferably evaluated by examining the subject's symptoms in a quantitative way, e.g., by noting a decrease in the frequency of adverse symptoms, behaviors, or attacks, or an increase in the time for sustained worsening of symptoms. In a successful treatment, the subject's status will have improved (i.e., frequency of relapses will have decreased, or the time to sustained progression will have increased).

Based on the exemplary transdermal delivery systems (also referred to as transdermal devices or devices) described herein, a method for treating a suitable condition with an active agent is provided. In embodiments, devices comprising the active agent are useful for treating, delaying progression, delaying onset, slowing progression, preventing, providing remission, and improvement in symptoms of cognitive disorders or disease and of multiple sclerosis are provided herein. In embodiments, devices comprising the active agent are provided for maintaining mental function including, but not limited to a least one of maintaining thinking, memory, speaking skills as well as managing or moderating one or more behavioral symptoms of a cognitive disorder or disease. In embodiments, the cognitive disorder is Alzheimer's disease. In particular embodiments, the cognitive disorder is Alzheimer's type dementia. In embodiments, devices comprising memantine are provided for use in treating, etc. mild, moderate, or severe Alzheimer's disease. In other embodiments, devices comprising fingolimod are provided for use in treating multiple sclerosis, preventing and/or reducing frequency of relapses of multiple sclerosis, in particular of relapsing-remitting multiple sclerosis.

In one embodiment, the methods relate to therapy of CNS disorders or of autoimmune disorders in a subject in need thereof by contacting a tissue of the subject with one or more transdermal delivery systems. The terms "transdermal" and "topical" are used herein in the broadest sense to refer to administration of an active agent, e.g., memantine or donepezil or fingolimod, to the skin surface or mucosal membrane of an animal, including humans, so that the drug passes through the body surface, e.g., skin, and into the individual's blood stream. The term "transdermal" is intended to include trans-mucosal administration, i.e., administration of a drug to the mucosal (e.g., sublingual, buccal, vaginal, rectal) surface of an individual so that the agent passes through the mucosal tissue and into the individual's blood stream.

The terms "topical delivery system," "transdermal delivery system" and "TDS," which refer to the route of delivery of the drug via the skin tissue, are used interchangeably herein.

The terms "skin" tissue or "cutaneous" tissue as used herein are defined as including tissues covered by a stratum corneum, or stratum lucidum, and/or other mucous membranes. The term further includes mucosal tissue, including the interior surface of body cavities, e.g., buccal, nasal, rectal, vaginal, etc., which have a mucosal lining. The term "skin" should be interpreted as including "mucosal tissue" and vice versa.

The term "system," as used herein, is defined as an article, an apparatus or a device containing the active agent or a composition thereof for administration to the skin, local tissues under the skin, the circulation system or other sites or targeting the human body via skin permeation sites.

In some instances, the transdermal devices are configured with as a single layer comprising the active agent. By "single layer" is meant that the transdermal delivery device includes only a single layer of active agent containing matrix and does not include separate distinct layers for a pressure sensitive adhesive, transdermal active agent layer, etc. It will be appreciated the single layer devices may include one or more additional layers that do not include the active agent. In some embodiments, the transdermal delivery device includes at least a backing and an active agent-containing layer. The composition may further include a release liner.

In one embodiment, the delivery systems are multi-layered. As used herein, the term "multi-layer" refers to a transdermal delivery device comprising at least two or more layers comprising an active agent. As a representative example, a multi-layered device may contain two or more layers of drug-in-adhesive. The layers may be separated by a membrane from other layers. In this manner, one active agent layer may provide immediate release of the active and the other layer may provide control release of an active from the reservoir. In embodiments, multi-layered devices may optionally contain a release liner-layer and a backing. The rate of drug release from the various layers depends on membrane permeability and diffusion of drug molecules. One non-limiting example of a multi-layered patch is provided in FIG. 1A.

In embodiments, the transdermal delivery system comprises one or more drug reservoirs. The term "drug reservoir" means a composition made to retain and release a drug for transdermal delivery, which composition is produced by combining a drug and a matrix material. The drug reservoir can be a drug reservoir composition, a solid drug reservoir layer, a solid drug reservoir adhesive layer, or a liquid drug reservoir layer. In some embodiments, a drug reservoir can be a solid drug reservoir layer in a multi-laminate transdermal drug delivery medical device. When combined with an adhesive, the drug reservoir can also be a solid drug reservoir adhesive layer, which can be used, for example, in a monolith transdermal drug delivery medical device. The drug reservoir can also comprise permeation enhancers, plasticizers, and any other suitable additive, unless otherwise noted.

In one embodiment, the drug reservoir contains (a) a memantine compound, (b) an alkaline/basic salt, (c) one or more polymers, (d) a carrier, (e) a dissolving agent, optionally together with a permeation enhancer, and other agents such as gelling agents, emollients, surfactants, humectants, viscosity enhancers, emulsifiers, etc., listed below. The drug reservoir may also contain one or more (f) disintegrants. In embodiments, at least one of the one or more polymers is an acrylate copolymer.

In some embodiments, the drug reservoir comprises, as active ingredient, a memantine compound or a derivative thereof. Memantine (NAMENDA) is a compound that belongs to the admantane class of active agents. In some embodiments, the compound comprises the structure shown in Formula I. In another embodiment, the memantine compound is also known as 3,5-dimethyladamantan-1-amine; 1-amino-3,5-dimethyladamantane; 1,3-dimethyl-5-adamantanamine; 3,5-dimethyl-1-adamantanamine; 3,5-dimethyl-1-aminoadamantane; and 3,5-dimethyltricyclo(3.3.1.1(3,7))decan-1-amine:

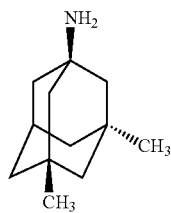

Formula I

The terms "compound" and "compounds" as used herein refers to a compound encompassed by the generic formulae disclosed herein, any subgenus of those generic formulae, and any specific compounds within the generic and subgeneric formulae. Particularly, "memantine" as used herein refers to the hydrochloride salt of 3,5-dimethyladamantan-1-amine.

In one embodiment, the transdermal delivery system according to the invention comprises memantine in the form of the free base, e.g., a compound whose empirical formula as a free base is $C_{12}H_{21}N$ (having a pKa of about 10.7). The term "free base" or "freebase" refers to the conjugate base (deprotonated) form of an amine, as opposed to its conjugate acid (protonated) form. The amine may be a primary amine (e.g., $RNH_2$, wherein R is an alkyl group), secondary amine (e.g., $R^1R^2NH$, wherein $R^1$ and $R^2$ are each, individually, the same or different alkyl groups) or tertiary amine (e.g., $R^1R^2R^3N$, wherein $R^1$, $R^2$ and $R^3$ are each, individually, the same or different alkyl groups).

In certain embodiments, the amine salt is converted into the base form in situ via a decomposition reaction. As used herein, the term "in situ" refers to processes, events, objects, or components that are present or take place within the context of the system or device, including, the surrounding environment, for example, the biological material with which the device is in contact with. As an example, an in situ reaction may refer to the reaction of the various components present in the device (e.g., memantine salt and bicarbonate), including, components provided by the human skin tissue (e.g., water, which allows the components to react in aqueous form by dissolving the memantine salt and bicarbonate). The term is contrasted with ex situ, which refers to outside of the environment.

In one embodiment, the decomposition reaction comprises reaction of a salt of memantine with an alkaline salt. An "alkaline salt" or "basic salt" as used herein refers to a salt, when dissolved in water, yields a solution with pH greater than 7.0. In some embodiments, the basic or alkaline salt is an inorganic salt of a weak acid, e.g., an alkali metal salt of a weak acid selected from the group consisting of sodium acetate, sodium borate, sodium metaborate, sodium carbonate, sodium bicarbonate, sodium phosphate, potassium carbonate, potassium bicarbonate, potassium citrate, potassium acetate, and potassium phosphate. In particular embodiments, the alkaline salt is one whose conjugate base from the weak acid hydrolyzes to form a basic solution. For example, in sodium carbonate ($Na_2CO_3$), the carbonate (conjugate base) from the carbonic acid (weak acid) hydrolyzes in water or other polar medium to form a basic solution. Representative examples of such alkaline salts include salts of $Li^+$, $Na^+$, $K^+$, $Rb^+$, $Mg^{2+}$, $Ca^{2+}$, $Sr^{2+}$, or $Ba^{2+}$, preferably $Na^+$, $K^+$, $Mg^{2+}$, $Ca^{2+}$, wherein the conjugate bases are, for e.g., sulfate ($SO_4^-$), nitrate ($NO_3^-$), dihydrogen phosphate ($H_2PO_4^-$), acetate ($CH_3COO^-$), oxalate, citrate, tartrate, hydrogen carbonate ($HCO_3^-$), carbonate ($CO_3^{2-}$), phosphate ($PO_4^{3-}$), hydrogen phosphate ($HPO_4^{2-}$), and hydrogen sulfide ($HS^-$).

Particularly, the salt is selected from an acetate, oxalate, citrate, tartrate, bicarbonate, or hydrogen sulfide salt of $Na^+$, $K^+$, $Mg^{2+}$, or $Ca^{2+}$, for e.g., $Na^+HCO_3^-$, $K^+HCO_3^-$, $Mg^{2+}(HCO_3^-)_2$ or $Na^+CH_3COO^-$, etc.

Purely as a representative example, wherein the salt is a bicarbonate salt, it undergoes in situ reaction with memantine HCl salt to release water, $CO_2$ and the free amine in the following manner:

$Me^x(HCO_3)_x + x*(R—NH_3^+Cl^-) \rightarrow Me^xCl_x + xH_2O + xCO_2 + xR—NH_2$, wherein Me is a metal (e.g., $Li^+$, $Na^+$, $K^+$, $Rb^+$, $Mg^{2+}$, $Ca^{2+}$, $Sr^{2+}$, or $Ba^{2+}$), x is the valency of the metal (e.g., from 1 to 3), R is the adamantane ring of memantine and $—NH_2$ is the amine group of memantine.

In one embodiment, the reaction takes place in a polar medium. In another embodiment, the reaction takes place in an amphipathic medium.

In another embodiment, a free base may be generated using other art-known techniques. For example, in one embodiment, the free base is generated from the salt using ion exchangers. Preferred anion exchange resins are commercially available resins containing basic (cationic) groups such as quaternary ammonium groups, tertiary sulphonium groups, quaternary phosphonium groups or alkyl pyridinium groups. Particularly preferred anion exchange resins are those containing quaternary amines, such as REXYN™ 201 (Fisher Scientific Co.), AMBERLITE™ IR A-400, (Mallinckrodt Chemical Works), IONAC™ A-540 (Matheson, Coleman and Bell), DOWEX™ I and 21K (Dow Chemical Co.), and DUOLITE™ A-101D and ES-109 (Diamond Shamrock Chemical Co.).

In another embodiment, the devices described herein comprise derivatives of the active agents. The term "derivative" as used herein includes salts, amides, esters, enol ethers, enol esters, acetals, ketals, orthoesters, hemiacetals, hemiketals, acids, bases, solvates, hydrates or prodrugs of the active agents. Such derivatives may be readily prepared by those of skill in this art using known methods for such derivatization. In certain embodiments, the derivatives may be administered to animals or humans without substantial toxic effects and either are pharmaceutically active or are prodrugs. Representative types of memantine derivatives are described in U.S. Pat. Nos. 3,391,142; 4,122,193; 4,273,774; and 5,061,703; U.S. Pat. Pub. Nos. 2004-0087658; 2005-0113458; 2006-0205822; 2009-0081259; 2009-0124659; and 2010-0227852; Eur. Pat. Pub. Nos. EP2260839A2; EP1682109B1; and Int. Pat. Pub. No. WO2005079779. For instance, antioxidant memantine derivatives containing N-acetyl-Cys-OH and N-acetyl-Cys (Allyl)-OH are described in Cacciatore et al., *Cent Nerv Syst Agents Med Chem.*, 2016 (PMID: 27356627).

In another embodiment, the devices comprise salts of the active agents. The term "salt" includes salts derived from a variety of organic and inorganic counter ions well known in the art and include, by way of example, hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt. In some embodiments, the salt of the compound is a hydrochloric acid salt. In some embodiments, the salt of the compound is formed by reacting the compound with an inorganic acid, e.g., hydrochloric acid, hydrobromic acid, sulfuric acid, phosphoric acid, or metaphosphoric acid. In some embodiments, the salt of the compound is formed by reacting the compound with an organic acid. In some embodiments, the salt of the compound is formed by reacting the compound with an organic acid, e.g., acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid.

In some embodiments, described herein is a hydrochloride salt of a compound that has the structure of Formula (I). In a particular embodiment, the memantine salt includes memantine hydrochloride.

In another embodiment, the device comprises solvent addition forms of the active agents, e.g., solvates and alcoholates. Solvates contain either stoichiometric or non-stoichiometric amounts of a solvent, and may be formed during the process of crystallization with acceptable solvents such as water, ethanol, and the like. Hydrates are formed when the solvent is water; alcoholates are formed when the solvent is alcohol. Solvates of compounds described herein can be conveniently prepared or formed using routine techniques. In one embodiment, the solvates comprise complexes of the memantine compound with one or more solvent (e.g., water or alcohol) molecules, or 1 to about 100, or 1 to about 10, or one to about 2, 3 or 4, solvent molecules per molecule of the memantine compound. In other embodiments, the compounds provided herein can exist in unsolvated as well as solvated forms.

In another embodiment, the devices comprise amides or esters of the active agents. The term "amide" refers to refers to either —$N(R^1)$—C(=O)— or —C(=O)—$N(R^1)$— wherein $R^1$ is defined herein to include hydrogen as well as other groups. The term "substituted amide" refers to the situation where R1 is not hydrogen, while the term "unsubstituted amide" refers to the situation where R1 is hydrogen. In one embodiment, the amide group is unsubstituted or substituted via the nitrogen atom by alkyl ($C_1$-$C_8$) group, aryl ($C_1$-$C_8$) group, phenyl, carbocyclic ($C_3$-$C_8$) group, heterocyclic ($C_3$-$C_8$) group, acyl, alkyl ($C_1$-$C_8$) halide, or alkenyl ($C_1$-$C_8$) group. The term "ester" refers to a chemical compound derived from an acid (organic or inorganic) in which at least one hydroxyl group is replaced by an alkoxy group. Representative types of "esters" include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

In another embodiment, the devices comprise isomers of the active agents. The term "isomer" includes compounds with the same formula but a different arrangement of atoms in the molecule. In embodiments, isomers of the memantine compounds are "tautomers" or "stereoisomers" of the compounds of Formula I. The term "stereoisomer" refers to compounds that differ in the chirality of one or more stereocenters. Stereoisomers include enantiomers and diastereomers. The term "tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles. Preferably, the tautomers and the stereoisomers of the compounds of Formula I have similar or same biological properties, e.g., with respect to NMDA receptor antagonism, as the parent memantine compounds.

In some embodiments, the devices comprise prodrugs of the active agents. The term "prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing a transdermally-administered compound to be more readily absorbed into the skin tissue) or which enhance delivery of the parent compound to a biological compartment (e.g., the brain) relative to the parent species. Prodrugs include amide and ester forms of the compounds of the invention. Examples of ester prodrugs include formate, acetate, propionate, butyrate, acrylate, and ethylsuccinate derivatives. A general overview of prodrugs is provided in Higuchi et al., *Pro drugs as Novel Delivery Systems*, Vol. 14 of the American Chemical Society Symposium Series and Edward B. Roche, ed., *Bioreversible Carriers in Drug Design*, American Pharmaceutical Association and Pergamon Press, 1987, both of which are incorporated herein by reference.

In some embodiments, the devices include mixtures of the active agents. The term "mixture" refers to a mingling together of two or more substances without the occurrence of a reaction by which they would lose their individual properties. In embodiments, a mixture may contain about 2, 3, 4, 5, or more of the aforementioned memantine compounds.

In one embodiment, the active ingredient is in micronized form. The term "micronized" refers to extremely fine particles that are a few microns in diameter. Methods for micronizing compounds are known in the art, e.g., jet milling pulverizing techniques disclosed in WO2011/070361. In one embodiment, the active ingredient is memantine HCl and the mean particle size of micronized memantine HCl is less than about 20 μm, particularly less than about 5 μm, and especially less than about 1 μm, e.g., about 0.5 μm or even about 0.1 μm.

In some embodiments, the active ingredient is a bicarbonate salt. Representative bicarbonate salts include, for example, sodium bicarbonate, potassium bicarbonate, ammonium bicarbonate, or a mixture thereof. Preferably, the bicarbonate salt is sodium bicarbonate.

In one embodiment, the active ingredient is in the ammonium ion form. Although the ionic form is more soluble in water (and blood) its passage through membranes is somewhat slower. Memantine, donepezil and fingolimod in the free base form (free amine) is lipophilic and is absorbed more readily through the skin cells and penetrates the dermal barrier faster than the salt forms (hydrophilic) of the drugs. In the devices and systems described herein, the conversion of the salt form of the drug into the free base form is accomplished in situ by providing the components, e.g., the bicarbonate and the memantine HCl together or in close proximity to each other. Optionally, a lipophilic solvent may be included to dissolve the more hydrophobic free base form of the drug. The other component(s) of the in situ synthetic process, e.g., polar or amphipathic medium, for carrying out the aqueous reaction, may be contained in the composition or provided externally.

In certain embodiments, the active compound and the bicarbonate salt, optionally together with any other ingredients or adjuvants, may be co-micronized together into a formulation. Methods for co-micronizing ingredients are known in the art. See, e.g., U.S. Pat. No. 5,424,077, which discloses a method of co-micronizing sorbitol, glycerol and potassium bicarbonate (0.05-0.5 μm particle size range) by an air jet mill procedure.

In the aforementioned embodiments, the drug reservoir may additionally comprise a carrier. As used herein, the term "carrier" includes emulsions, suspensions, gels, sols, colloids, and solids, designed for delivery of the aforementioned drugs In some embodiments, the carriers and/or excipients include, but are not limited to, alcohols, particularly polyhydroxy alcohols such as propylene glycol, polyethylene glycol, glycerol, and vegetable and mineral oils. The carriers and/or excipients can be added in various concentrations and combinations to form solutions, suspensions, oil-in-water emulsions or water-in-oil emulsions. In certain embodiments, the carrier and/or excipient is a polar solvent material selected from the group consisting of $C_3$-$C_4$ diols, $C_3$-$C_6$ triols, and mixtures thereof, and/or a polar lipid material selected from the group consisting of fatty alcohol esters, fatty acid esters. A mixture of the polar solvent material and the lipid material, for example, in a weight ratio of solvent material to the lipid material of about 60:40 to about 99:1, may also be used. Other suitable carriers are provided in U.S. Pat. No. 5,026,556.

In one embodiment, the carrier is a composition comprising two or more alcohols. Under this embodiment, the carrier may comprise, e.g., a mixture of octydodecanol and glycerol, wherein the weight ratio of octydodecanol and glycerol is between about 2:1 to 1:2, between about 3:2 to 2:3, between about 10:7 to 7:10, or about 1:1. Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, wherein the carrier comprises octydodecanol and glycerol, the composition may include other elements, e.g., buffers, surfactants, emollients and the like. In one embodiment, the carrier is a hydrophilic solvent. In one embodiment, the hydrophilic solvent is glycerol. In one embodiment, the hydrophilic solvent is present in the drug reservoir in an amount between 1-30 wt %, 2-30 wt %, 2-20 wt %, 5-25 wt %, 5-20 wt %, 5-15 wt %, 7-15 wt %, 7-12 wt %, and 8-12 wt %.

In another embodiment, the carrier consists essentially of two or more alcohols. In yet another embodiment, the carrier consists of two alcohols. By "consisting of" is meant including, and limited to, whatever follows the phrase "consisting of." Thus, the phrase "consisting of" indicates that the listed elements are required or mandatory. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

In certain embodiments, the carriers may be buffered. In one embodiment, the carriers are buffered with alkaline buffers, e.g., ammonium buffer. In another embodiment, the carriers are buffered with acidic buffers, e.g., ethanoates, citrates, lactates, acetates, etc. In another embodiment, the buffered carriers contain zwitterionic buffers, such as, glycine, alanine, valine, leucine, isoleucine and phenylalanine, TRIS, MES, ADA, ACES, PIPES, MOPSO, cholamine chloride, MOPS, BES, TES, HEPES, DIPSO, MOBS, TAPSO, acetamidoglycine, TEA, POPSO, HEPPSO, EPS, HEPPS, Tricine, TRIZMA, Glycinamide, Glycyl-glycine, HEPBS, Bicine, TAPS, AMPB, CHES, AMP, AMPSO, CAPSO, CAPS, and CABS. Methods of formulating buffered compositions, e.g., via use of a properly calibrated pH probe, are known in the art.

In certain embodiments, the drug reservoir and/or contact adhesive may optionally further contain one or more surfactants. Examples of suitable additional surfactants include, for example, anionic surfactants, cationic surfactants, amphoteric surfactants, zwitterionic surfactants, non-ionic surfactants, and combinations thereof. Specific examples of suitable surfactants are known in the art and include those suitable for incorporation into the delivery device. The drug reservoir and/or contact adhesive may suitably include one or more surfactants in an amount from about 0.01% by weight to about 2% by weight of the layer or device. When one or more surfactants is employed, the amount present will vary depending on the particular surfactant chosen, the particular mode of administration (e.g., dermal or mucosal) and the effect desired.

The drug reservoir and/or contact adhesive may also further contain one or more emulsifiers. Suitable emulsifiers include, but are not limited to, natural fatty acids, esters and alcohols and their derivatives, and combinations thereof. Other examples of suitable emulsifiers include nonionics such as polysorbate 20, polysorbate 80, anionics such as DEA phosphate, cationics such as behentrimonium methosulfate, and the like. The one or more emulsifiers may be included in the layer or device in an amount from about 0.01% by weight to about 2% by weight.

The drug reservoir and/or contact adhesive may include one or more agents that increase viscosity chosen in quantities that preferably do not irritate the skin and increase the retention time. Suitable agents include, but are not limited to, methylcellulose, carboxymethylcellulose sodium, ethylcellulose, carrageenan, carbopol, and/or combinations thereof. In embodiments, the agent that increases viscosity is included in the layer or device in quantities of from about 0.1% to about 10% by weight.

The devices or systems may also include additional ingredients, such as acceptable surfactants, co-solvents, adhesives, and agents to adjust the pH and osmolarity.

The device or system may additionally include adjunct components conventionally found in pharmaceutical compositions in their art-established fashion and at their art-established levels. For example, the compositions may contain additional compatible pharmaceutically active materials for combination therapy, e.g., donepezil (ARICEPT®), memantine, rivastigmine (EXCELON®), galantamine (RAZADYNE®), icopezil, pyridostigmine, edrophonium, neostigmine, physostigmine, Huperzine A, phenserine, tacrine, including, L-type calcium channel blocker selected from amlodipine, felodipine, isradipine, lacidipine, lercanidipine, nicardipine, nifedipine, nimodipine, nitrendipine, nisoldipine, or (+) isopropyl 2-methoxyethyl 4-(2-chloro-3-cyano-phenyl)-1,4-dihydro-2,6-dimethylpyridine-3,5-dicarboxylate, or a combination thereof. See, U.S. pat. Pub. No. 2009/0156639.

In embodiments, the one or more ingredients of at least the drug reservoir and/or the contact adhesive are of pharmaceutical grade, e.g., formulated with the purity and consistency that is expected for clinical testing and/or medical use.

In one specific embodiment, a method for treatment of a CNS disorder comprising administering to a subject in need thereof a transdermal delivery system comprising an adhesive matrix comprising (i) donepezil base or memantine base generated in situ by reaction of a salt of donepezil or memantine with an alkaline salt; (ii) a carrier and (iii) an acrylate polymer. In one specific embodiment, the carrier is glycerol. In embodiments, the salt is the halide salt (e.g., chloride, bromide, iodide), especially a hydrochloride salt of the active agent. In embodiments, the alkaline/basic salt is a bicarbonate salt of an alkali metal or an alkali earth metal, such as $Na^+$ or $K^+$. In embodiments, the carrier is a glycol, such as a glycol selected from glycerol, propylene glycol, and liquid polyethylene glycol. In embodiments, the dissolving agent is a higher alcohol, e.g., a $C_{10-30}$ alcohol such as a monovalent saturated or unsaturated aliphatic alcohol, wherein the hydrocarbyl group moiety is a straight chain or branched. In some embodiments the higher alcohol has a melting point of at least 40° C. The $C_{10-30}$ higher alcohol used herein includes, e.g., lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, sitosterol, phytosterol, lanosterol, lanolin alcohol, hydrogenated lanolin alcohol, and so forth. In embodiments, a higher alcohol is selected from lauryl alcohol, isostearyl alcohol, octyldodecanol and oleyl alcohol. The disintegrant may be selected from polyvinylpyrrolidone (PVP) or polyvinyl alcohol (PVA), including cross-linked derivatives thereof such as polyvinylpolypyrrolidone. The acrylate polymer may be a copolymer of acrylic acid/vinyl acetate selected from the hydroxyl group-containing polyacrylates. In one embodiment, the acrylate copolymer is manufactured from a monomer composition of vinyl acetate, 2-ethylhexyl-acrylate, hydroxyethyl acrylate and glycidyl acrylate (DUROTAK® 2287). Other components, such as plasticizers, permeation enhancers, surfactants, etc. can also be included, and in some embodiments these components include triethyl citrate, glycerol, sorbitan monolaurate, an α-hydroxy acid enhancer (e.g., an ester of lactic acid or glycolic acid, i.e., lauryl lactate).

In embodiments, the drug reservoir comprises at least about 0.1% by weight relative to the weight of the entire reservoir of the active agent, including, at least 0.5%, at least 1%, at least 2%, at least 5%, at least 10%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40% or greater % by weight, wherein all values are relative to the weight of the entire drug reservoir. In embodiments, the % weight of the active agent in the drug reservoir is between about 10-50 wt %, 10-30 wt %, 15-30 wt % or 15-25 wt % of the weight of the entire reservoir.

In some embodiments, the drug reservoir comprises a basic/alkali salt, e.g., bicarbonate salt, in an amount of at least about 0.1% by weight relative to the weight of the entire reservoir, including, at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, or greater % by weight, wherein all values are relative to the weight of the entire reservoir. In embodiments, the % weight of the alkali salt in the drug reservoir is between about 0.1-20 wt %, 0.1-15 wt %, 0.1-12 wt %, 0.5-15 wt %, 0.5-12 wt %, 0.5-5 wt %, 1-5 wt %, or 6%-12 wt %, based on the weight of the entire reservoir.

In some embodiments, the drug reservoir comprises the carrier, e.g., a glycol alcohol such as glycerol, in an amount that is at least about 0.1% by weight relative to the weight of the entire reservoir, including, at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, or greater % by weight, wherein all values are relative to the weight of the entire reservoir. In embodiments, the % weight of the carrier in the drug reservoir is between about 5%-15% of the weight of the entire reservoir.

In embodiments, the drug reservoir comprises the dissolving agent, e.g., a higher alcohol such as octyldodecanol, in an amount that is at least about 0.1% by weight relative to the weight of the entire reservoir, including, at least 0.5%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, or greater % by weight, wherein all values are relative to the weight of the entire reservoir. In embodiments, the drug reservoir comprises the dissolving agent in an amount between about 5%-15%, especially about 8%-12%, of the weight of the entire reservoir. In another embodiment, the % weight of the dissolving agent in the drug reservoir is between about 2%-10%, especially about 7%-8%, of the weight of the entire reservoir.

In embodiments, the amount of the disintegrant, e.g., polyvinylpyrrolidone (PVP) or polyvinyl alcohol (PVA), including cross-linked derivatives thereof, in the drug reservoir is at least about 1% by weight relative to the weight of the entire reservoir, including, at least about 4%, e.g., about 5%, about 6%, about 7%, about 8%, about 9%, about 10%, about 11%, about 12%, about 13%, about 14%, about 15%, about 16%, about 17%, about 18%, about 19%, about 20%, about 25%, about 26%, about 27%, about 28%, about 29%, about 30%, or greater % by weight, wherein all values are relative to the weight of the entire reservoir. In embodiments, the % weight of the disintegrant in the drug reservoir is between about 10%-20%, especially about 12%-18%, of the weight of the entire reservoir.

In embodiments, the drug reservoir comprises an acrylate polymer, e.g., a copolymer of acrylic acid/vinyl acetate selected such as hydroxyl group-containing polyacrylates, including cross-linked derivatives thereof, at least about 5% by weight relative to the weight of the entire reservoir, including, at least about 8%, about 10%, about 12%, about 14%, about 16%, about 18%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 45%, about 50%, or greater % by weight, wherein all values are relative to the weight of the entire reservoir. In embodiments, the % weight of the acrylate polymer in the drug reservoir is between about 20%-45%, especially about 30%-40%, of the weight of the entire reservoir.

The amount of each of the optional ingredients, e.g., permeation enhancers, gelling agents, emollients, surfactants, humectants, viscosity enhancers, emulsifiers, may individually range from about 0.1% to about 10% by weight of the entire reservoir, including, about 0.2%, about 0.4%, about 0.6%, about 0.8%, about 1.0%, about 1.5%, about 2.0%, about 2.5%, about 3.0%, about 3.5%, about 4.0%, about 4.5%, about 5.0%, about 6.0%, about 6.5%, about 7.0%, about 7.5%, about 8.0%, about 9.0%, about 10%, or greater % by weight, wherein all values are relative to the weight of the entire reservoir.

A drug reservoir comprised of a composition as described herein and hereinabove is contemplated for use in a transdermal delivery system, where the system additionally comprises a skin contact adhesive. The skin contact adhesive layer may be fabricated from any of the adhesive materials listed herein. In one embodiment, the skin contact adhesive comprises a higher alcohol and a biocompatible polymer.

In one embodiment, the skin contact adhesive layer comprises a $C_{10-30}$ higher alcohol. In embodiments, the higher alcohol is selected from the group consisting of lauryl alcohol, isostearyl alcohol, octyldodecanol, and oleyl alcohol. In one embodiment, the skin contact adhesive does not include a hydrophilic solvent that is present in the drug reservoir.

In one embodiment, the amount of the higher alcohol, e.g., octyldodecanol, in the skin contact adhesive layer is at least about 1% by weight relative to the weight of the adhesive layer, including, at least about 4%, e.g., about 5%, about 6%, about 7%, about 8%, about 9%, about 10%, about 11%, about 12%, about 13%, about 14%, about 15%, about 16%, about 17%, about 18%, about 19%, about 20%, or greater % by weight, wherein all values are relative to the weight of the adhesive layer. In embodiments, the % weight of the higher alcohol in the adhesive layer is between about 5%-15%, especially about 8%-12%, of the entire adhesive layer.

In one embodiment, the skin contact adhesive layer comprises a biocompatible polymer which is polyisobutylene (PIB), a silicone polymer, acrylate copolymers, butyl rubber, polybutylene, styrene-iosprene-styrene block copolymers, styrene-butadiene-styrene block copolymers, ethylene-vinyl acetate (EVA), mixtures and copolymers thereof. Particularly, the biocompatible polymer is polyisobutylene.

In one embodiment, the biocompatible polymer is a PIB-based matrix comprising PIB Oppanol B100 (BASF, MW=1,100,000), PIB Oppanol B 12 (BASF, MW=51,000, MW/MN 3.2) and polybutene (PB) Indopol H1900 (INEOS oligomers, MW=4500, MW/MN=1.8). The weight ratio between components of the PIB matrix is as follows: PIB Oppanol B100:PIB Oppanol B 12:Indopol H1900=10:50: 40. See, Brantseva et al., *European Polymer Journal*, 76, 228-244, 2016.

In one embodiment, the skin contact adhesive layer comprises about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.9, or greater % by weight of one or more biocompatible polymers, wherein all values are relative to the weight of the adhesive layer. Particularly, the % weight of the polymer in the adhesive layer is between about 50%-90%, especially about 60%-80%, of the entire adhesive layer.

In some embodiments, the skin contact adhesive layer optionally comprises highly dispersive silica, e.g., hydrophobic colloidal silica that can effectively adsorb hydrophobic drugs and other hydrophobic ingredients. By using hydrophobic colloidal silica at a certain percentage as an excipient (from about 3% to about 20%, preferably from about 5% to about 10% in the formulation), the diffusion of the active ingredient through the matrix can be controlled during storage. Examples of the dispersive silica for use in the compositions include, but are not limited to, the high purity amorphous anhydrous colloidal silicon dioxide for use in pharmaceutical products sold under the name AEROSIL®, e.g., AEROSIL®90, AEROSIL®130, AEROSIL®150, AEROSIL®200, AEROSIL®300, AEROSIL®380, AEROSIL®OX50, AEROSIL®TT600, AEROSIL®MOX80, AEROSIL®COK84, AEROSIL®R202, AEROSIL®R805, AEROSIL®R812, AEROSIL®812S, AEROSIL®R972, and/or AEROSIL® R974 or any other highly disperse silica, especially AEROSIL®200 and/or AEROSIL®R972 can be used according to the invention as highly disperse silica.

In one embodiment, the skin contact adhesive layer comprises highly dispersive silica at least about 40% by weight relative to the weight of the entire adhesive layer, including, at least about 1% by weight relative to the weight of the adhesive layer, including, at least about 3%, e.g., about 4%, about 5%, about 6%, about 7%, about 8%, about 9%, about 10%, about 11%, about 12%, about 13%, about 14%, about 15%, about 16%, about 17%, about 18%, about 19%, about 20%, or greater % by weight, wherein all values are relative to the weight of the entire adhesive layer.

In some embodiments, the skin contact adhesive layer optionally comprises a matrix modifier. Without wishing to be bound by theory, it is believed that the matrix modifier facilitates homogenization of the adhesive matrix. Sorption of hydrophilic moieties is a possible mechanism for this process. Thus, known matrix modifiers which are to some degree water-sorbent may be used. For example, possible matrix modifiers include colloidal silicone dioxide, fumed silica, cross-linked polyvinylpyrrolidone (PVP), soluble PVP, cellulose derivatives (e.g. hydroxypropyl cellulose (HPC), hydroxyethylcellulose (HEC)), polyacrylamide, polyacrylic acid, a polyacrylic acid salt, or a clay such as kaolin or bentonite. An exemplary commercial fumed silica product is Cab-O-Sil (Cabot Corporation, Boston, Mass.). The hydrophilic mixtures described in U.S. Published Patent Application No. 2003/0170308 may also be employed, for example mixtures of PVP and PEG or of PVP, PEG, and a water-swellable polymer such as the polymethacrylate-based copolymers sold under the trade name EUDRAGIT, and in particular EUDRAGIT® L100-55.

In embodiments, the matrix modifier is individually included in the contact adhesive layer in an amount between about 1-40%, about 10-30%, about 15-25%, about 5-7%, about 7-20%, or about 7-25% relative to the weight of the adhesive matrix (inclusive of sub-ranges), including, at least about 3%, e.g., about 4%, about 5%, about 6%, about 7%, about 8%, about 9%, about 10%, about 11%, about 12%, about 13%, about 14%, about 15%, about 16%, about 17%, about 18%, about 19%, about 20%, or greater % by weight, wherein all values are relative to the weight of the entire adhesive layer. In some embodiments, the matrix modifier does not include ethylcellulose.

In some embodiments, a hydrophobic drug (e.g., memantine) and other hydrophobic ingredients may be adsorbed to the hydrophobic surface of the silica particles using art-known technology. In such embodiments, the hydrophobic colloidal silica has a large specific surface area for drug deposition, as well as exhibiting strong adsorption to hydrophobic drugs.

In one embodiment, the skin contact adhesive layer as manufactured does not include a pharmaceutically active agent intended for systemic delivery. However, the skin contact adhesive layer when fabricated into a transdermal delivery system and stored for a period of time and/or during use may contain the pharmaceutically active agent due to diffusion of the agent from the drug reservoir adhesive matrix into the skin contact adhesive layer.

The penetration or permeation enhancer in either or both of the skin contact adhesive layer and the drug reservoir adhesive matrix may be chosen from a wide range of such compounds known in the art. In some embodiments, permeation enhancers for use in the adhesive matrix include, but are not limited to, methyl laurate, propylene glycol monolaurate, glycerol monolaurate, glycerol monooleate, lauryl lactate, myristyl lactate, and dodecyl acetate. Additional permeation enhancers are described in U.S. Pat. No. 8,874,879, which is incorporated herein by reference. It will be appreciated that the compositions herein may include one or more or at least one permeation enhancer. In embodiments, the penetrating or permeating enhancer is included in an amount between about 1-10%, about 2-5%, about 2-10% relative to the weight of the adhesive matrix.

Either or both of the skin contact adhesive layer and the drug reservoir adhesive matrix may further include other conventional additives such as adhesive agents, antioxidants, crosslinking or curing agents, pH regulators, pigments, dyes, refractive particles, conductive species, antimicrobial agents, opacifiers, gelling agents, viscosity modifiers or thickening agents, stabilizing agents, and the like as known in the art. In those embodiments wherein adhesion needs to be reduced or eliminated, conventional detackifying agents may also be used. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. These additives, and amounts thereof, are selected in such a way that they do not significantly interfere with the desired chemical and physical properties of the adhesive and/or active agent.

Either or both of the skin contact adhesive layer and the drug reservoir adhesive matrix may further may also contain irritation-mitigating additives to minimize or eliminate the possibility of skin irritation and/or skin damage resulting from the drug, the enhancer, or other components of the composition. Suitable irritation-mitigating additives include, for example: α-tocopherol; monoamine oxidase inhibitors, particularly phenyl alcohols such as 2-phenyl-1-ethanol; glycerol; salicylic acids and salicylates; ascorbic acids and ascorbates; ionophores such as monensin; amphiphilic amines; ammonium chloride; N-acetylcysteine; cis-urocanic acid; capsaicin; chloroquine; and corticosteroids.

In the method, a transdermal delivery system is provided that is comprised of a therapeutic agent and a reservoir comprising the therapeutic agent. The therapeutic agent (i) has a half-life in the blood when delivered orally of greater than about 48 hours and (ii) is for the treatment of a chronic condition. Upon application of the transdermal delivery system to the skin of a subject, transdermal delivery of the therapeutic agent occurs, to provide a systemic blood concentration of the agent (or a metabolite) that at steady state is bioequivalent to administration of the therapeutic agent orally. As discussed below, bioequivalency is established by (a) a 90% confidence interval of the relative mean Cmax and AUC of the therapeutic agent administered from the transdermal delivery system and via oral delivery between 0.70 and 1.43 or between 0.80 and 1.25, or (b) a 90% confidence interval of the geometric mean ratios for AUC and Cmax of the therapeutic agent administered from the transdermal delivery system and via oral delivery between 0.70 and 1.43 or between 0.80 and 1.25.

In embodiments, bioequivalency is established by (a) a 90% confidence interval of the relative mean Cmax and AUC of the therapeutic agent administered from the transdermal delivery system and via oral delivery are between about 0.60 and 1.30, between about 0.7 and 1.43 or between 0.8 and 1.25, or (b) a 90% confidence interval of the geometric mean ratios for AUC and Cmax of the therapeutic agent administered from the transdermal delivery system and via oral delivery are between 0.60 and 1.30, between about 0.7 and 1.43 or between 0.8 and 1.25. In some embodiments, the 90% confidence ratio for establishing bioequivalency is between about 0.60 to 1.25, between about 0.6 to 1.0, between about 0.70 to 1.30, between about 0.70 to 1.25, between about 0.70 to 1.0, between about 0.80 to 1.30, between about 0.80 to 1.25, between about 0.80 to 1.0, between about 0.90 to 1.30, between about 0.90 to 1.25, between about 0.90 to 1.0, between about 1.0 to 1.30, between or about 1.0 to 1.25.

Therapeutic agents with half-lives of greater than about 48 hours are readily identified by skilled artisans from various reference books and publications (see, for example, Schulz et al., *Critical Care*, 16:R136 2012). Examples include carbamazepine, anidulafungin, amphotericin, clonazepam, clozapine, digoxin, ethosuximide, maprotiline, mephobarbital, nortriptyline, olanzapine, phenobarbital, sirolimus, zonisamide, memantine, donepezil, fingolimod, and others.

In one embodiment, the therapeutic agent is a poorly water soluble agent or a sparingly water soluble agent. The term "sparingly water-soluble" is understood as comprising the terms described in the pharmacopeias for water solubilities of drugs such as "of low solubility", "slightly soluble", "very slightly soluble" to "practically insoluble". By way of example, the free base of memantine has a water solubility of 0.9 mg/mL. The free base of donepezil has a water solubility of 2.9 mg/L. Both are considered poorly water soluble.

The method is based on a finding that transdermal delivery system for drugs with a long blood elimination half life can be designed to provide a pharmacokinetic (PK) profile that is bioequivalent to oral administration of the same drug, at about the same dose. Standard PK parameters routinely used to assess the behavior of a dosage form in vivo (in other words when administered to an animal or human subject) include $C_{max}$ (peak concentration of drug in blood plasma), $T_{max}$ (the time at which peak drug concentration is achieved) and AUC (the area under the plasma concentration vs time curve). Methods for determining and assessing these parameters are well known in the art. The desirable pharmacokinetic profile of the transdermal delivery systems described herein comprise but are not limited to: (1) a $C_{max}$ for transdermally delivered form of the drug when assayed in the plasma of a mammalian subject following administration, that is bioequivalent to the $C_{max}$ or an orally delivered or an intravenously delivered form of the drug, administered at the same dosage; and/or (2) an AUC for transdermally delivered form of the drug when assayed in the plasma of a mammalian subject following administration, that is preferably bioequivalent to the AUC for an orally delivered or an intravenously delivered form of the drug, administered at the same dosage; and/or (3) a $T_{max}$ for transdermally delivered form of the drug when assayed in the plasma of a mammalian subject following administration, that is within about 80-125% of the $T_{max}$ for an orally delivered or an intravenously delivered form of the drug, administered at the same dosage. Preferably the transdermal delivery system exhibits a PK profile having a combination of two or more of the features (1), (2) and (3) in the preceding sentence. Alternatively, the transdermal delivery system exhibits a PK profile having one or both of the features (1) and (2).

In the field of pharmaceutical development the term "bioequivalence" will be readily understood and appreciated by the person skilled in the art. Various regulatory authorities have strict criteria and tests for assessing whether or not two drug products are bioequivalent. These criteria and tests are commonly used throughout the pharmaceutical industry and the assessment of bioequivalence is recognized as a standard form of activity in drug development programs where the characteristics and performance of one product are being compared to those of another product. Indeed in seeking approval to market certain types of products (e.g. those evaluated under the FDA's "Abbreviated New Drug Application" procedure), it is a requirement that the follow-on product be shown to be bioequivalent to a reference product.

In one embodiment of the invention, the method encompasses providing and/or administering a transdermal delivery system comprising a therapeutic agent with a long blood circulation half-life that when transdermally administered to a subject in a fasted state is bioequivalent to administration of the agent orally or intravenously to a subject also in a fasted state, in particular as defined by $C_{max}$ and AUC guidelines given by the U.S. Food and Drug Administration and the corresponding European regulatory agency (EMEA). Under U.S. FDA and Europe's EMEA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). Europe's EMEA previously used a different standard, which required a 90% CI for AUC between 0.80 to 1.25 and a 90% CI for $C_{max}$ between 0.70 to 1.43. Methods for determining $C_{max}$ and AUC are well known in the art.

Figure 1B:
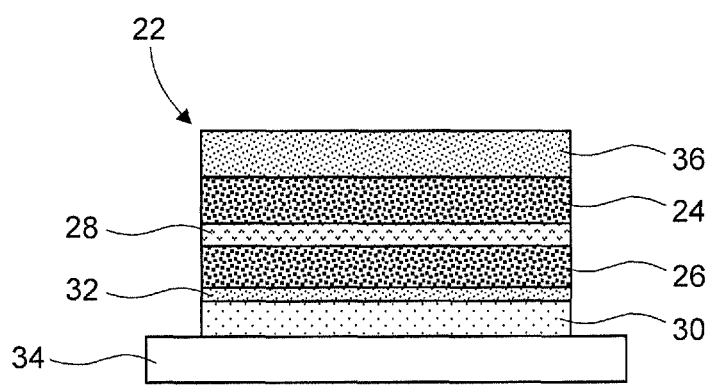
Figure 1C:
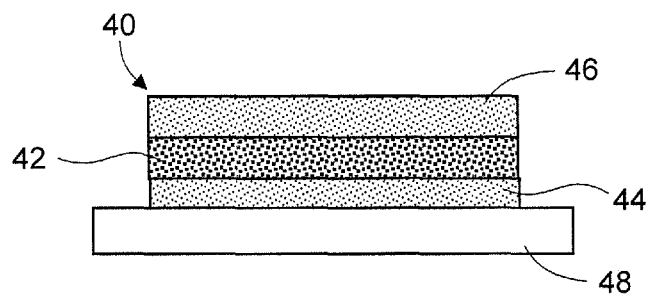

The transdermal delivery system contemplated may have a variety of configurations, and several non-limiting examples are depicted in FIGS. 1A-1C. FIG. 1A illustrates a transdermal delivery system 10 comprised of a drug reservoir 12 and a contact adhesive 14 separated by a rate controlling membrane or by a non-rate controlling material, such as a tie layer composed of a non-woven polyester or polypropylene, 16. A backing layer 18 and a release liner 20 are also present. FIG. 1B illustrates a second embodiment of a transdermal delivery system 22 comprised of a first drug reservoir 24 and a second drug reservoir 26, the first and second drug reservoirs separated by a non-rate controlling material, such as a tie layer composed of a non-woven polyester or polypropylene, 28. A contact adhesive layer 30 provides for attachment of the system to the skin of a user, where a rate controlling membrane 32 controls release of therapeutic agent from the second drug reservoir into the contact adhesive and ultimately onto the skin of a user. A release liner 34 and a backing layer 36 are also present. FIG. 1C shows another embodiment of a transdermal delivery system 40 comprised of a drug reservoir 42 and a contact adhesive layer 44 that provides for attachment of the system to the skin of a user. A backing layer 46 and a release liner 48 are also present.

In a study conducted in support of the claimed invention, a transdermal delivery system comprising donepezil was prepared and tested. As described in Example 1, the transdermal delivery system comprised a drug reservoir and a contact adhesive with a rate controlling membrane situated between the drug reservoir and the contact adhesive, as depicted in FIG. 1A. A drug reservoir in the form of a solid monolithic adhesive reservoir was prepared using an acrylic acid/vinyl acetate copolymer adhesive with a solvent mixture that included a hydrophilic solvent (glycerol) and a permeation enhancer. In one embodiment, the solvent mixture is comprised of glycerol, and lauryl lactate, and optionally further includes triethyl citrate and sorbitan monolaurate. The drug reservoir contained approximately 5 wt % donepezil hydrochloride and sodium bicarbonate, to generate in situ donepezil base. A contact adhesive layer comprised of the same acrylic acid/vinyl acetate copolymer adhesive, along with triethyl citrate, lauryl lactate and ethyl acetate was prepared. A rate controlling membrane, to control the diffusional release of donepezil base from the drug reservoir, separated the drug reservoir and the contact adhesive.

In one embodiment, the microporous membrane comprises a plurality of pores. The plurality of pores in the microporous membrane contains a solvent or a solvent composition. In one embodiment, the solvent composition in the pores of the microporous membrane is comprised of one or more of the solvents present in either or both of the drug reservoir and the contact adhesive. For example, an exemplary solvent composition contained in the pores of the microporous membrane is one or more of triethyl citrate, a surfactant, and a permeation enhancer. Another exemplary embodiment is a solvent composition comprised of one or more of triethyl citrate, sorbitan monolaurate, and lauryl lactate. In one embodiment, the solvent composition comprises between 40-80 wt % triethyl citrate, between 5-40 wt % lauryl lactate and between 5-25 wt % sorbitan laurate. In another embodiment, the solvent composition comprises between 50-75 wt % or 55-70 wt % triethyl citrate, between 10-35 wt % or 15-30 wt % lauryl lactate and between 8-20 wt % or between 10-15 wt % sorbitan laurate. In another embodiment, the solvent in the pores of the microporous membrane is octyldodecanol. In one embodiment, the solvent composition or solvent contained in the pores of the microporous membrane excludes the hydrophilic solvent present in the drug reservoir. In one embodiment, the solvent composition contained in the pores of the microporous membrane excludes glycerin.

The microporous membrane may be pretreated with the solvent composition so that its pores are saturated with, filled with, or partially filled with the solvent or solvent composition. The microporous membrane is, in one embodiment, a polypropylene microporous membrane and may have an average pore size in the range of about 0.001 μm to about 100 μm, about 1 μm to about 10 μm, about 0.010 μm to about 0.100 μm, or about 0.040 μm to about 0.050 μm. For example, the average pore size can be about 0.035 μm, 0.036 μm, 0.037 μm, 0.038 μm, 0.039 μm, 0.040 μm, 0.041 μm, 0.042 μm, 0.043 μm, 0.044 μm, 0.045 μm, 0.046 μm, 0.047 μm, 0.048 μm, 0.049 μm, or 0.050 μm. In some embodiments, the microporous membrane has an average pore size of about 0.043 μm. The microporous membrane is, in one embodiment, a polypropylene microporous membrane and has a porosity in the range of about 30% to about 50%, about 35% to about 45%, or about 40% to about 42%. For example, the microporous membrane can have a porosity of about 30%, 31%, 32%, 33%, 34%, 35%, 36%, 37%, 38%, 39%, 40%, 41%, 42%, 43%, 44%, 45%, 46%, 47%, 48%, 49%, or 50%.

Accordingly, in one embodiment, a transdermal delivery system for systemic delivery of donepezil is provided, wherein the transdermal delivery system comprises a salt form of donepezil and a weak base in the drug reservoir is provided, to generate in situ the base form of donepezil that is delivered via the skin for systemic uptake. In another embodiment, the transdermal delivery system also comprises one or more of triethyl citrate, lauryl lactate, glycerol and sorbitan laurate in the drug reservoir, and one or more of triethyl citrate, lauryl lactate and sorbitan laurate in a contact adhesive. In one embodiment, the drug reservoir and the contact adhesive each comprise one or more of triethyl citrate, lauryl lactate and sorbitan laurate. The triethyl citrate may be present in one or both of the drug reservoir and the contact adhesive in an amount between about 1-20 wt %, 2-25 wt %, 5-15 wt %, 5-12 wt %, 7-15 wt %, 7-12 wt %, 8-12 wt %, 9-12 wt %, 1-8 wt %, 1-6 wt %, 1-5 wt %, 1.5-5 wt %, 2-5 wt %, 2.5-5 wt %, 2.5-4.5 wt %. Ethyl acetate may be present in one or both of the drug reservoir and the contact adhesive in an amount between about 25-60 wt %, where in one embodiment, a greater amount of ethyl acetate is present in the drug reservoir than in the contact adhesive, where the drug reservoir comprises 1.2, 1.3, 1.4, 1.5, 1.6, 1.7 or 1.8 times more ethyl acetate than the contact adhesive layer. Sorbitan laurate may be present in one or both of the drug reservoir and the contact adhesive in an amount between about 0.01-5 wt % or 0.1-5 wt %, where in one embodiment, sorbitan laurate is present in the drug reservoir and in the contact adhesive in the same amounts (on a w/w basis of the total amount in each layer individually, e.g., the amount in weight percent in the drug reservoir layer is the same as the amount in weight percent in the contact adhesive layer). In another embodiment, one or both of the drug reservoir and the contact adhesive comprise lauryl lactate in an amount between about 0.1-10 wt %, 0.5-8 wt % or 0.5-7 wt %, 1-10 wt %, 1-7 wt %, 1-5 wt %, 1.5-5 wt %, 2-5 wt %, 2.5-5 wt %, 0.25-5 wt %, 0.5-5 wt % or 0.5-4 wt %, 0.5-4.5 wt %. In one embodiment, the drug reservoir comprises an amount of lauryl lactate that is equal to or within about 0.5%, 1%, 5 wt %, 10 wt %, 15 wt % or 20 wt % of the amount of lauryl lactate present in the contact adhesive layer.

The transdermal delivery system prepared according to Example 1 was tested in vivo for systemic delivery of donepezil, as described in Example 2. In this in vivo study, six human subjects received treatment with a transdermal delivery system applied to their skin and worn for one week, and then removed. Another group of six human subjects were treated with orally administered donepezil (ARICPET®) at a dose of 5 mg taken on day one and on day 7 of the study. Blood samples were taken from the subjects and plasma concentrations of donepezil determined. The results are shown in FIGS. 2A-2B.

Figure 2A:
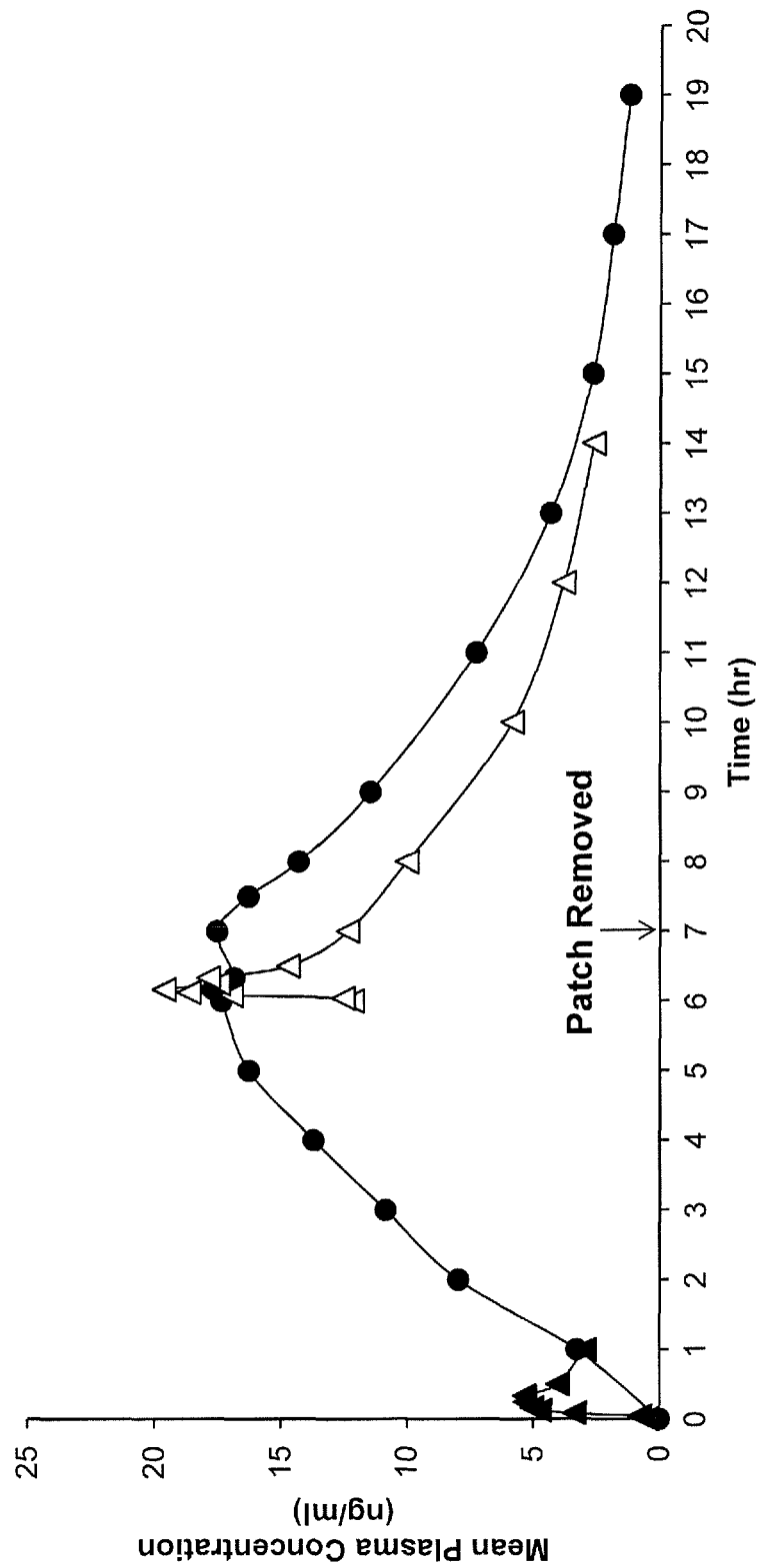
FIG. 2A is a graph of mean plasma concentration of donepezil, in ng/mL, as a function of time, in days, in human subjects treated with a donepezil transdermal delivery system (circles) for 1 week, or with 5 mg of donepezil administered orally on day 1 and on day 7 (triangles)

FIG. 2A shows the mean plasma concentration of donepezil, in ng/mL, in human subjects treated with a donepezil transdermal delivery system (circles) for 1 week, or with 5 mg of donepezil administered orally on day 1 and on day 7 (triangles). The donepezil transdermal delivery system provided a plasma concentration bioequivalent to the plasma concentration provided from oral delivery of a similar dose of donepezil. Accordingly, in one embodiment, a method of administering donepezil transdermally is provided by administering a transdermal delivery system that provides a pharmacokinetic profile that is bioequivalent to the pharmacokinetic profile obtained by oral administration of donepezil.

Figure 2B:
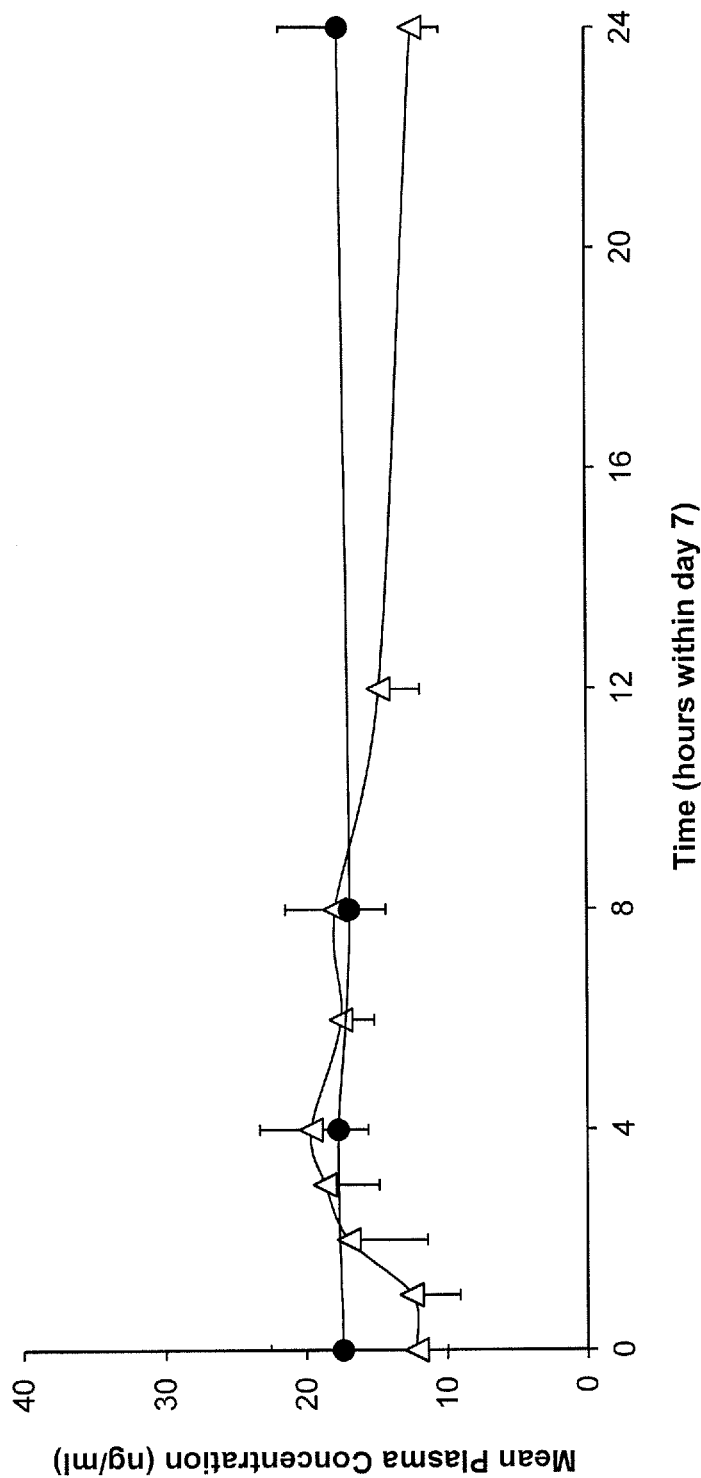
FIG. 2B is a graph showing the mean plasma concentration of donepezil, in ng/mL, in the 24 hour period after oral administration of a 5 mg donepezil tablet (triangles) and after removal of the donepezil transdermal delivery system (circles)

FIG. 2B is a graph showing a close up of the data points from FIG. 2A in the 24 hour period after oral administration of the 5 mg donepezil tablet (triangles) and after removal of the donepezil transdermal delivery system (circles). The transdermal delivery system provides a sustained, constant donepezil plasma concentration for 24 hours after its removal, similar to that observed in the 24 hour post oral administration.

Figure 3:
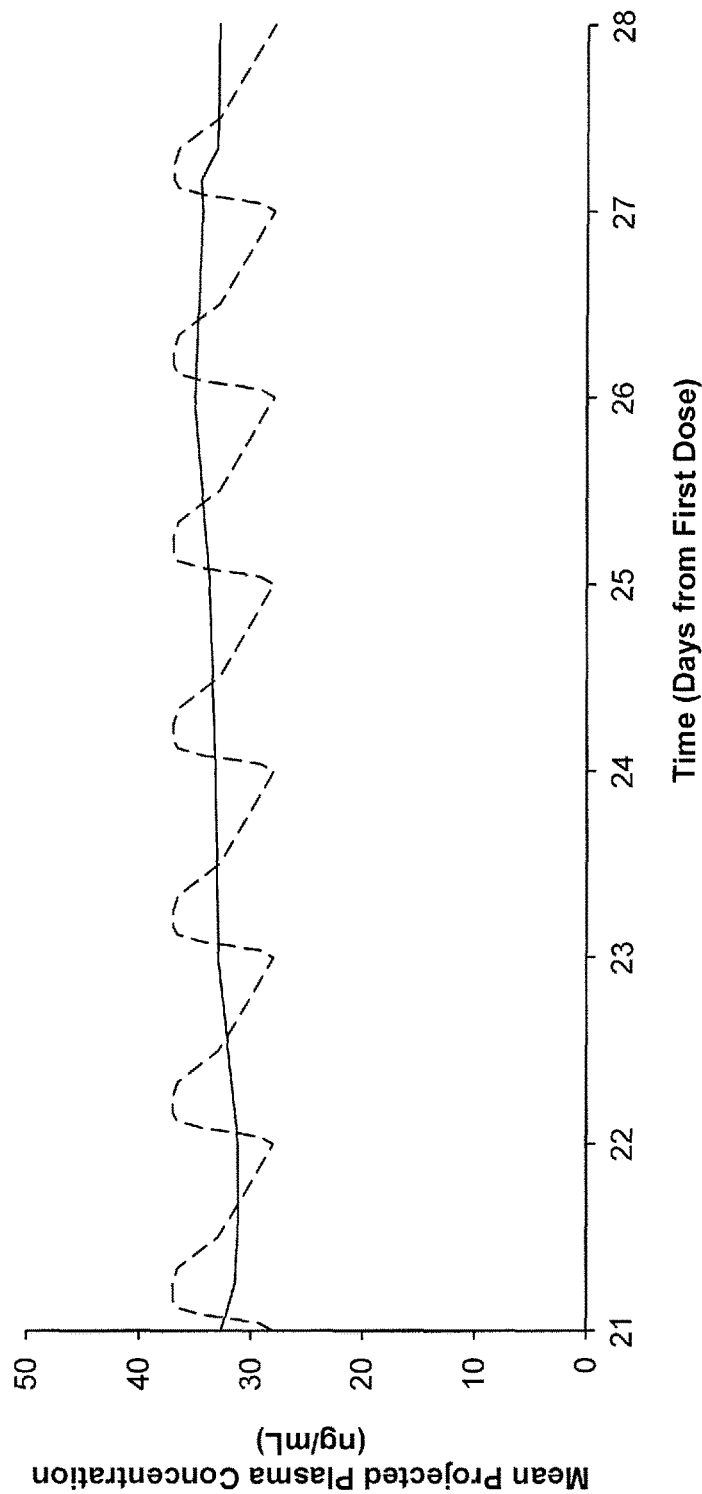
FIG. 3 is a graph showing the projected mean plasma concentration of donepezil, in ng/mL, over a 28 day (4 week) treatment period with a transdermal delivery system designed to administer 10 mg/day for a week (solid line), with a new patch applied once weekly, and over a 28 day period with a 10 mg daily oral tablet of donepezil (dashed line)

FIG. 3 is a graph showing the projected mean plasma concentration of donepezil, in ng/mL, over a 28 day (4 week) treatment period with a transdermal delivery system designed to administer 10 mg/day for a week (solid line) and over a 28 day period with a 10 mg daily oral tablet of donepezil (dashed line). The plasma fluctuations resulting from oral administration are eliminated by the transdermal system, where a fresh patch is applied each week and a constant plasma concentration is maintained over the treatment period. The transdermal delivery system provides a constant plasma concentration of donepezil for a sustained period of time (e.g., 3 days, 5 days, 7 days, 14 days), where the plasma concentration is essentially the same as or within about 10%, 15%, 20% or 30% of the plasma concentration achieved with daily oral administration of a similar daily dose of donepezil.

Figure 4:
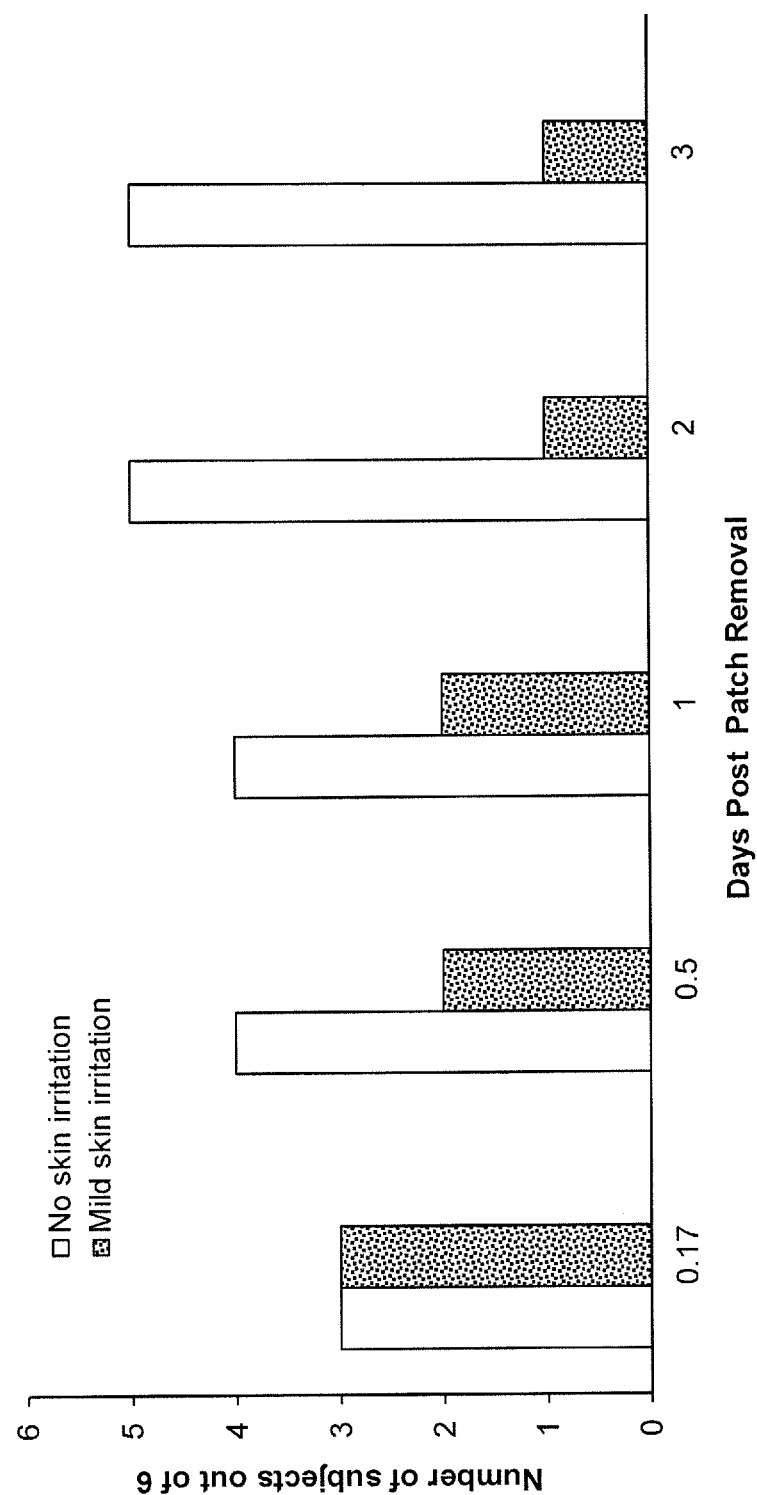
FIG. 4 is a bar graph of the number of subjects in the group treated with the donepezil transdermal delivery system for 1 week and the observed skin irritation subsequent to patch removal, where the open bars indicate no skin irritation and the filled bars indicate mild skin irritation.

With reference again to the study in Example 2, the six subjects treated with a donepezil transdermal delivery system for one week were monitored for several days following removal of the delivery system from their skin for signs of skin irritation. FIG. 4 is a bar graph showing the number of subjects out of the 6 in the group and the observed skin irritation in the period after removal of the delivery system, where the open bars indicate no skin irritation and the filled bars indicate mild skin irritation. The delivery system resulted in no or mild skin irritation in the hours after removal, and any mild irritation resolved with a day or two.

In another study, human subjects were treated with a transdermal delivery system designed to deliver systemically an amount of donepezil that is bioequivalent to orally administered donepezil at a 10 mg, once daily dose. The projected pharmacokinetic parameters Cmax, AUC and Cmin for the two routes of delivery are compared in Table 1.

TABLE 1

Projected Pharmacokinetic Parameters

| PK Parameter at Steady State | Once-weekly transdermal delivery system | 10 mg oral donepezil, once daily | Geometric Mean Ratio (transdermal:oral) |
|---|---|---|---|
| Geometric mean $C_{max}$ (ng/ml) | 40.6 | 45.6 | 0.890 |
| Geometric mean $C_{min}$ (ng/ml) | 34.2 | 30.8 | 1.110 |
| Geometric mean $AUC_{week}$ (ng-hr/ml) | 6367 | 6165 | 1.033 |

Accordingly, in one embodiment, a method for delivering a therapeutic agent to a subject is provided. The method comprises providing a transdermal delivery system comprised of a therapeutic agent and a reservoir comprising the therapeutic agent, wherein the therapeutic agent (i) has a half-life in the blood when delivered orally of greater than about 48 hours and (ii) is for the treatment of a chronic condition, and administering or instructing to administer the transdermal delivery system to the skin of a subject. The method achieves transdermal delivery of the therapeutic agent that is bioequivalent to administration of the therapeutic agent orally, wherein bioequivalency is established by (a) a 90% confidence interval of the relative mean Cmax and AUC of the therapeutic agent administered from the transdermal delivery system and via oral delivery between 0.70 and 1.43 or between 0.80 and 1.25, or (b) a 90% confidence interval of the geometric mean ratios for AUC and Cmax of the therapeutic agent administered from the transdermal delivery system and via oral delivery between 0.70 and 1.43 or between 0.80 and 1.25. In one embodiment, the therapeutic agent is donepezil.

In another study, a transdermal delivery system for systemic delivery of memantine was prepared. As described in Example 3, transdermal delivery systems comprising memantine base were prepared. The delivery systems were comprised of an adhesive drug reservoir comprising 4% memantine base, 65% permeation enhancers in 51% adhesive matrix. The permeation enhancers were ethyl acetate, isopropyl alcohol, propylene glycol, and levulinic acid. In one embodiment, a memantine transdermal delivery system comprised of a permeation enhancer selected from ethyl acetate, octyldodecanol and levulinic acid is contemplated. In one embodiment, the memantine transdermal delivery system comprises between about 25-50 wt % ethyl acetate, preferably between about 25-40 wt %. In another embodiment, the memantine transdermal delivery system comprises between about 15-40 wt % levulinic acid, preferably between about 20-30 wt %. In another embodiment, the memantine transdermal delivery system comprises between about 3-15 wt % octyldodecanol, preferably between about 3-10 wt %.

The transdermal delivery systems prepared according to Example 3 were tested in vivo for systemic delivery of memantine as described in Example 4. In this in vivo study, human subjects received treatment with a transdermal delivery system applied to their skin and worn for either three days or for one week, and then removed. Another group of human subjects were treated with orally administered memantine (NAMENDA XR®) at a dose of 28 mg taken on day one and on day 7 of the study. Blood samples were taken from the subjects and plasma concentrations of memantine determined. The results are shown in FIGS. 5A-5B.

Figure 5A:
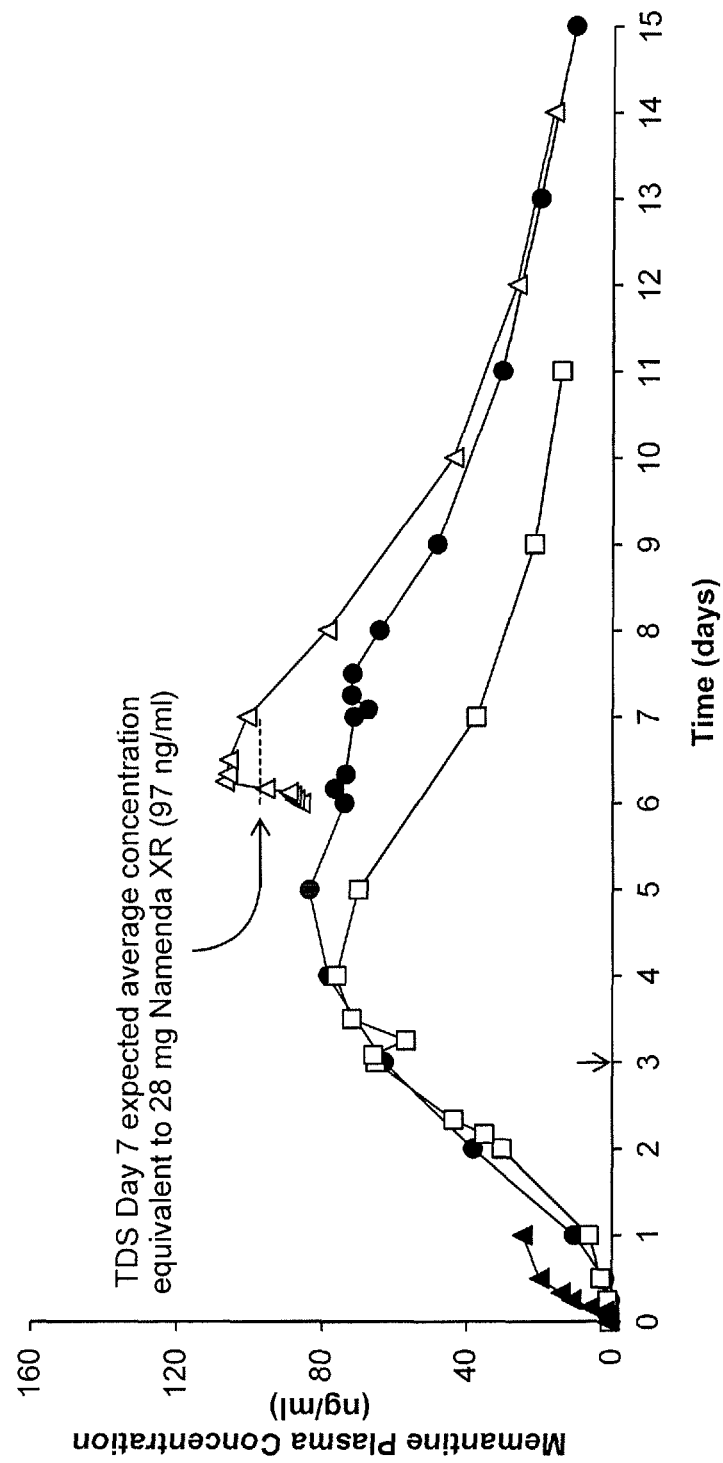
FIG. 5A shows the mean plasma concentration of memantine, in ng/mL, in human subjects treated with a memantine transdermal delivery system for 1 week (circles) or for 3 days (squares), or with 28 mg of memantine administered orally on day 1 and on day 7 (triangles)

FIG. 5A shows the mean plasma concentration of memantine, in ng/mL, in human subjects treated with a memantine transdermal delivery system for 1 week (circles) or for 3 days (squares), or with 28 mg of memantine administered orally on day 1 and on day 7 (triangles). Accordingly, in one embodiment, a method of administering memantine transdermally is provided by administering a transdermal delivery system that provides a pharmacokinetic profile that is bioequivalent to the pharmacokinetic profile obtained by oral administration of memantine.

Figure 5B:
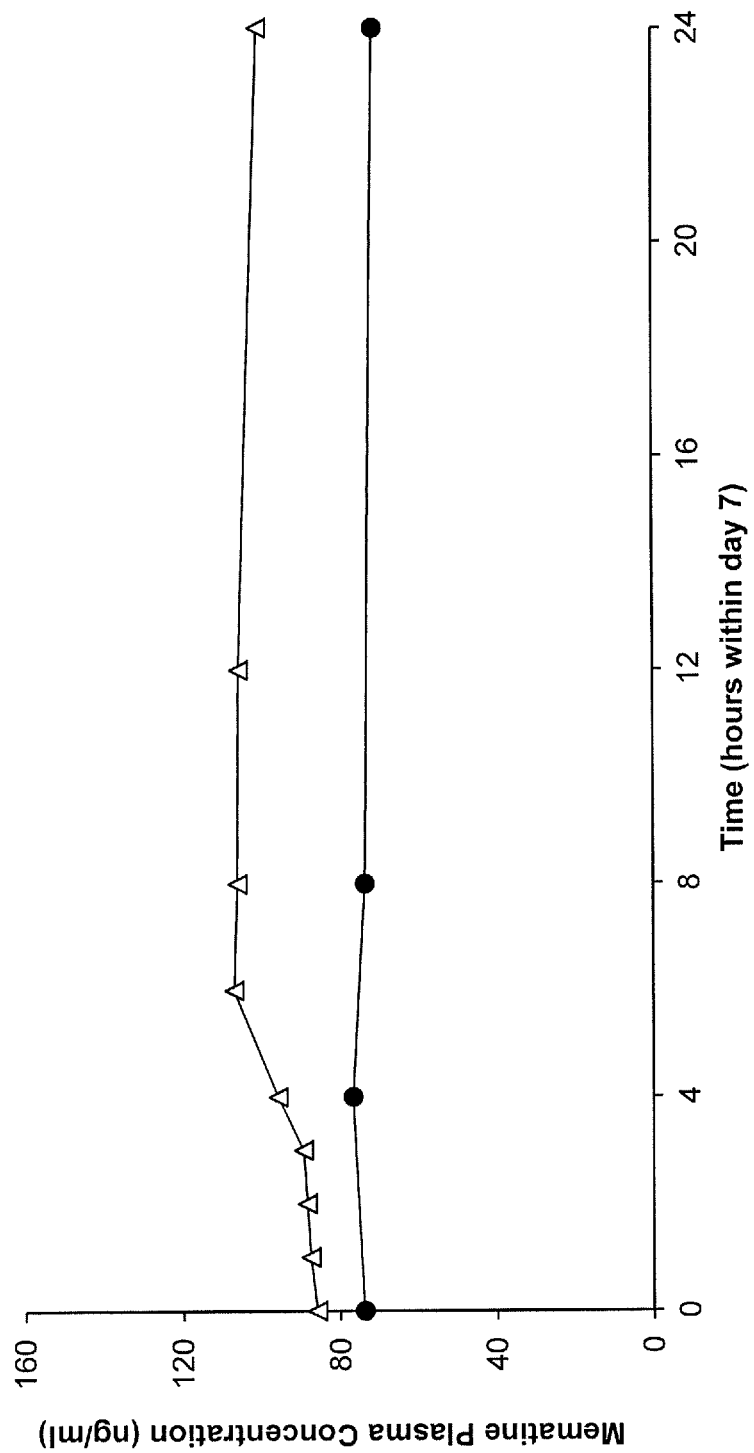
FIG. 5B is a graph showing the mean plasma concentration of memantine, in ng/mL, in the 24 hour period after oral administration on day 7 of the study of a 28 mg memantine tablet (triangles) and after removal of the memantine transdermal delivery system worn for 1 week (circles)

FIG. 5B is a graph showing the data points from FIG. 5A in the 24 hour period after oral administration of the 28 mg memantine tablet (triangles) and after removal of the memantine transdermal delivery system that was worn for 1 week (circles). The transdermal delivery system provides a sustained, constant memantine plasma concentration for 24 hours after its removal, similar to that observed in the 24 hour post oral administration.

Figure 6A:
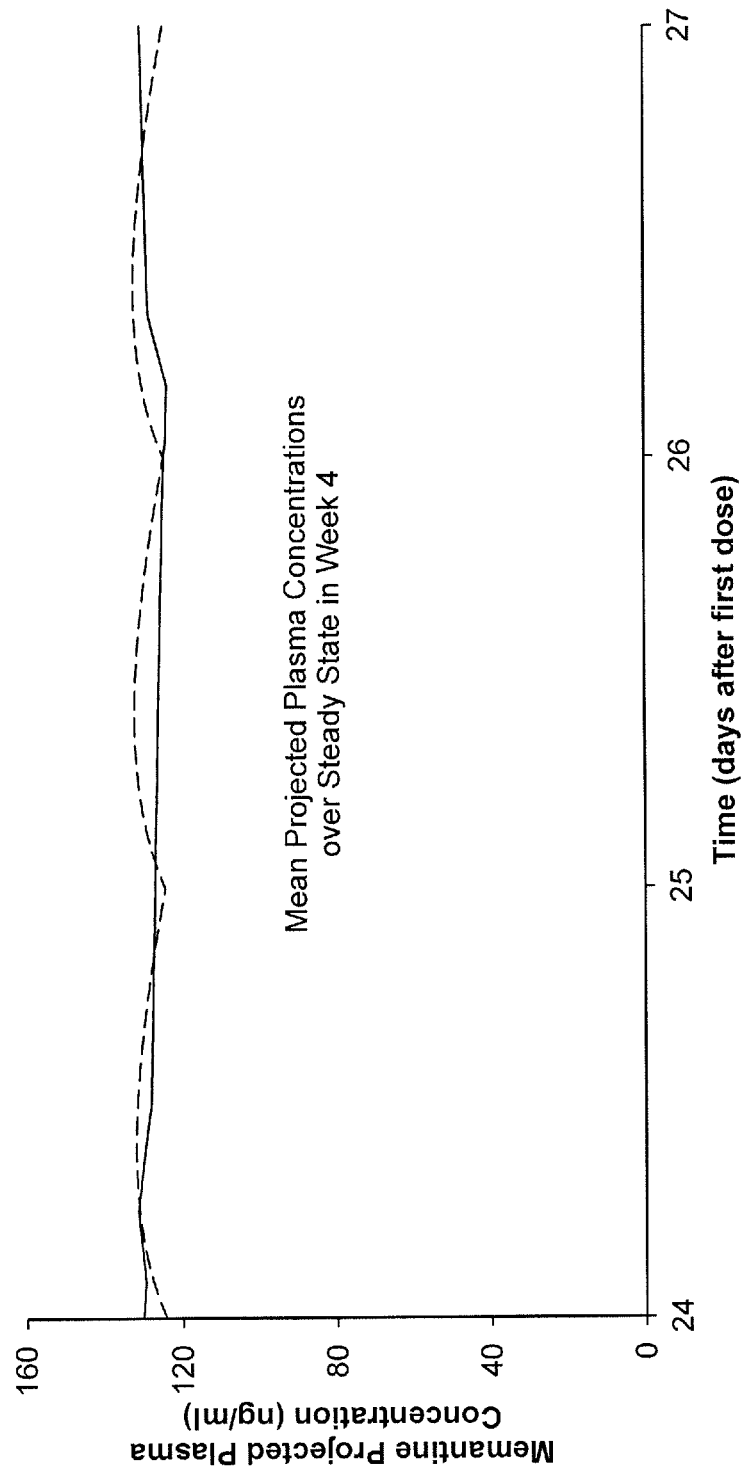
FIG. 6A is a graph showing the projected mean plasma concentration of memantine, in ng/mL, on days 24-28 following treatment with (1) a transdermal delivery system designed to administer 28 mg/day for 3 days (solid line), with a new patch applied every third day from days 1-24, (2) a 28 mg daily oral tablet of memantine (dashed line)

FIG. 6A shows the projected mean plasma concentration of memantine, in ng/mL, on days 24-28 following treatment with (1) a transdermal delivery system designed to administer 28 mg/day for 3 days (solid line), with a new patch applied every third day from days 1-24, (2) a 28 mg daily oral tablet of memantine (dashed line). The transdermal delivery system provides a constant plasma concentration of memantine for a sustained period of time (e.g., 3 days, 5 days, 7 days, 14 days), where the plasma concentration is essentially the same as or within about 10%, 15%, 20% or 30% of the plasma concentration achieved with daily oral administration of a similar daily dose of memantine.

Figure 6B:
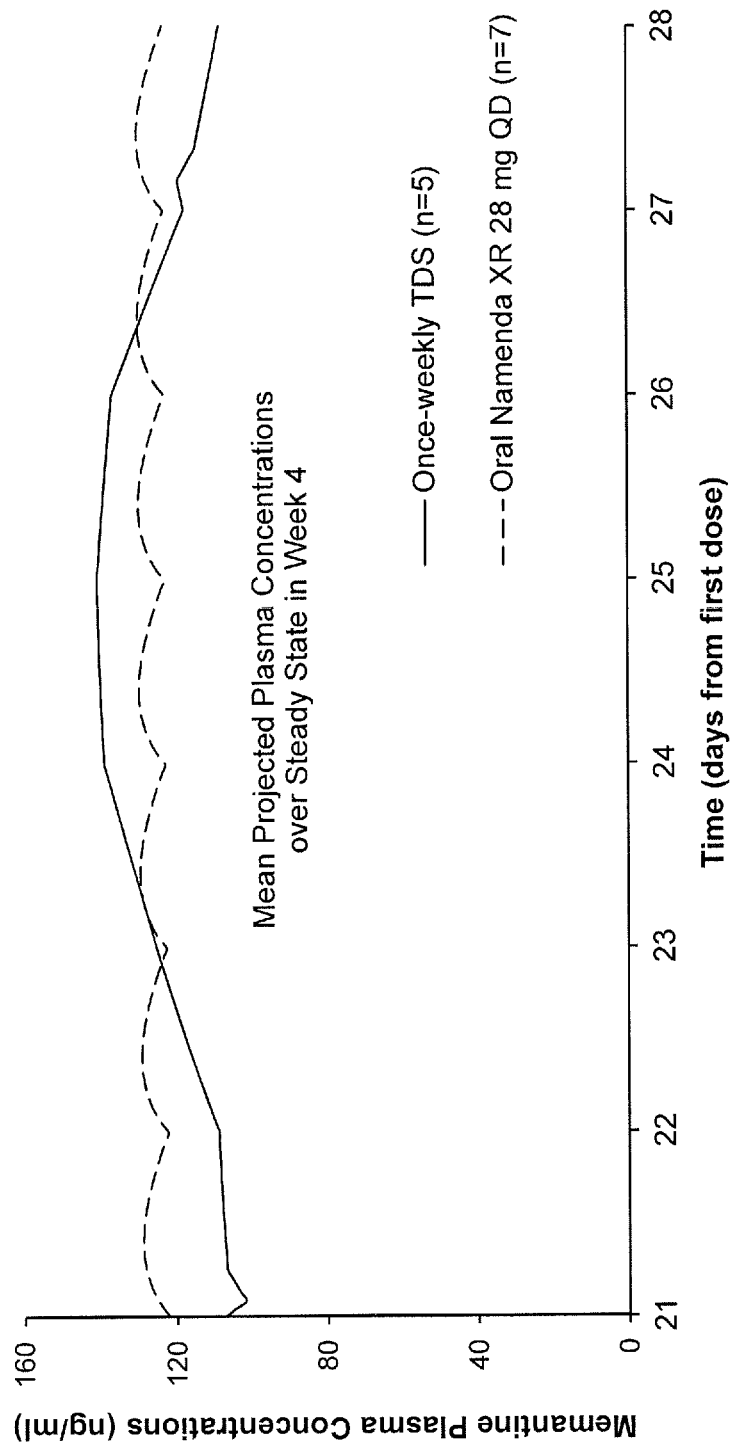
FIG. 6B is a graph showing the projected mean plasma concentration of memantine, in ng/mL, on days 21-28 following treatment with (1) a transdermal delivery system designed to administer 28 mg/day for 7 days (solid line), with a new patch applied every seventh day for 4 weeks, (2) a 28 mg daily oral tablet of memantine (dashed line)

FIG. 6B is a graph showing the projected mean plasma concentration of memantine, in ng/mL, on days 21-28 following treatment with (1) a transdermal delivery system designed to administer 28 mg/day for 7 days (solid line), with a new patch applied every seventh day for 4 weeks, (2) a 28 mg daily oral tablet of memantine (dashed line). The transdermal delivery system provides a constant plasma concentration of memantine for a sustained period of time (e.g., 3 days, 5 days, 7 days, 14 days), where the plasma concentration is essentially the same as or within about 5%, 10%, 15%, 20% or 30% of the plasma concentration over the sustained period of time achieved with daily oral administration of a similar daily dose of memantine.

Example 7 describes transdermal delivery systems comprising memantine that were prepared in another study in support of the method claimed herein. The transdermal systems were prepared with a drug reservoir comprised of memantine hydrochloride and sodium bicarbonate, with octyldodecanol as a dissolving agent. Glycerol was added as a carrier, and the components were mixed into an adhesive matrix of an acrylate copolymer, polyisobutylene and cross-linked polyvinylpyrrolidone. The weight percent of the components in each layer of the transdermal delivery systems are summarized in Tables 7.1 and 7.2, in Example 7 below.

Figure 7A:
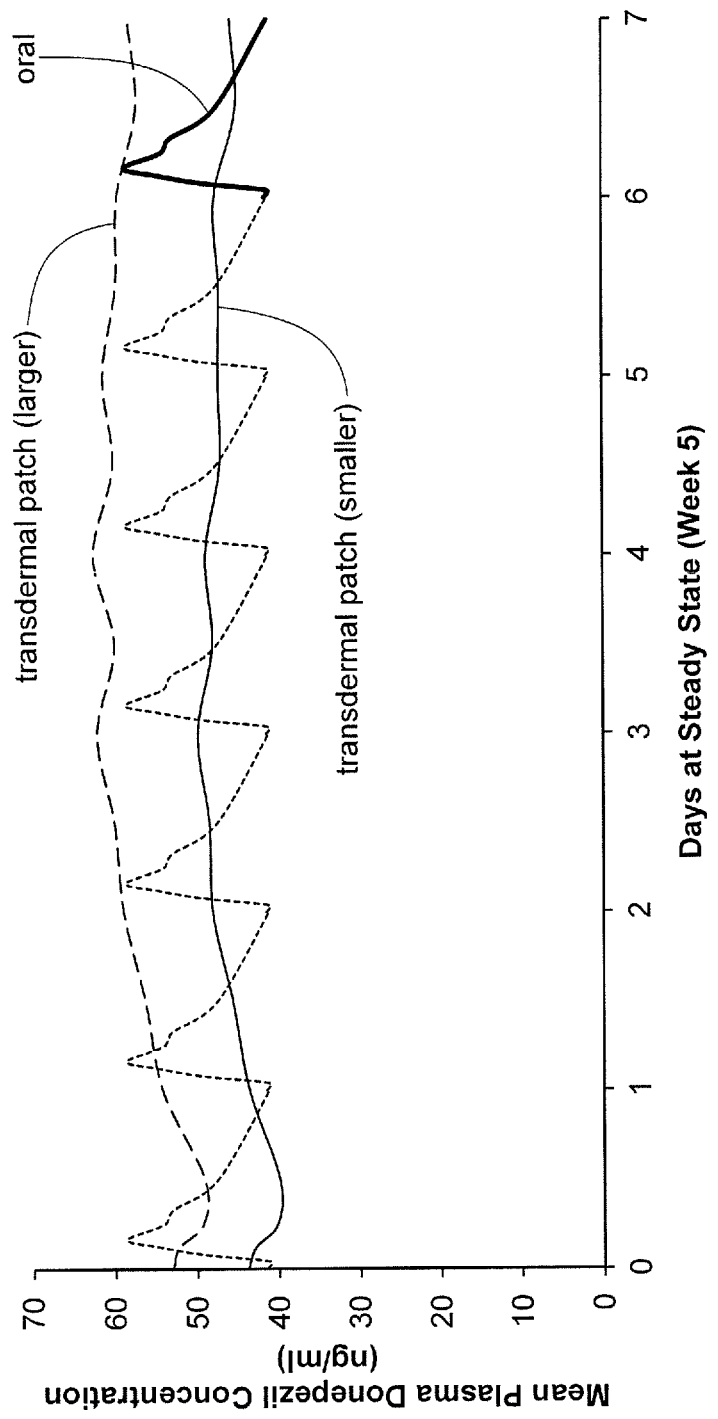
FIG. 7A shows the mean plasma concentration of donepezil, in ng/mL, at each day in the fourth week (week 5) of a clinical human study where subjects were treated with donepezil administered transdermally from transdermal patch with a first surface area (solid line) and a second, larger surface area (dashed line) and donepezil administered orally, where the donepezil plasma concentration for patients treated orally is indicated by the thick, bold line at days 6-7, and the dotted line shows the projected daily plasma concentration for oral treatment.

Examples 8 and 9 below describe a study conducted on human subjects where transdermal patches comprising donepezil were studied and compared to orally administered donepezil. In this study, patients were enrolled to participate in a six month, three-period, randomized crossover study comparing the steady-state pharmacokinetic profiles of once-daily oral donepezil (ARICEPT®) with a donepezil transdermal patch formulation. The transdermal patch was provided in two sizes, A and B, yet other than surface area, the transdermal patches were the same in all respects. During the study, the 60 enrolled participants received one week of 5 mg/day of donepezil, followed by 4 weeks of 10 mg/day of donepezil delivered from the once-weekly transdermal patch. Pharmacokinetic measurements were evaluated during the fourth week of the 10 mg/day treatment, when plasma concentrations had achieved steady levels. Blood samples for the subjects receiving the transdermal treatment were taken daily throughout the fourth week to determine pharmacokinetics. Subjects receiving oral donepezil had blood drawn on the last day of the fourth week to determine pharmacokinetics. The mean plasma concentration of donepezil, in ng/mL, is shown in FIG. 7A, for each day in the fourth week of the study (week 5), where the solid line corresponds to the transdermal patch with a smaller surface area and the dashed line corresponds to the transdermal patch with a larger surface area. The thick, bold line at days 6-7 shows the mean plasma concentration for the subjects receiving the oral donepezil, and the dotted line shows the projected daily plasma concentration for oral treatment. The mean plasma concentrations of donepezil in the subjects treated with a transdermal patch were bioequivalent to the plasma concentration of donepezil in the subject treated orally with donepezil. The larger and smaller transdermal patches demonstrated dose proportionality. Table 2 shows the primary pharmacokinetic parameters in a bioequivalence assessment of the smaller surface area transdermal patch used in the study.

TABLE 2

| Primary Pharmacokinetic Parameter | Geometric Mean Ratio (%) of smaller patch to oral dose | Bioequivalence Limits (target 80-125%) |
| --- | --- | --- |
| AUC (ng-hr/mL) | 104.7% | 95.2-115.2 |
| $Cmax_{ss}$ (ng/mL) | 91.6% | 83.1-100.8 |

Figure 7B:
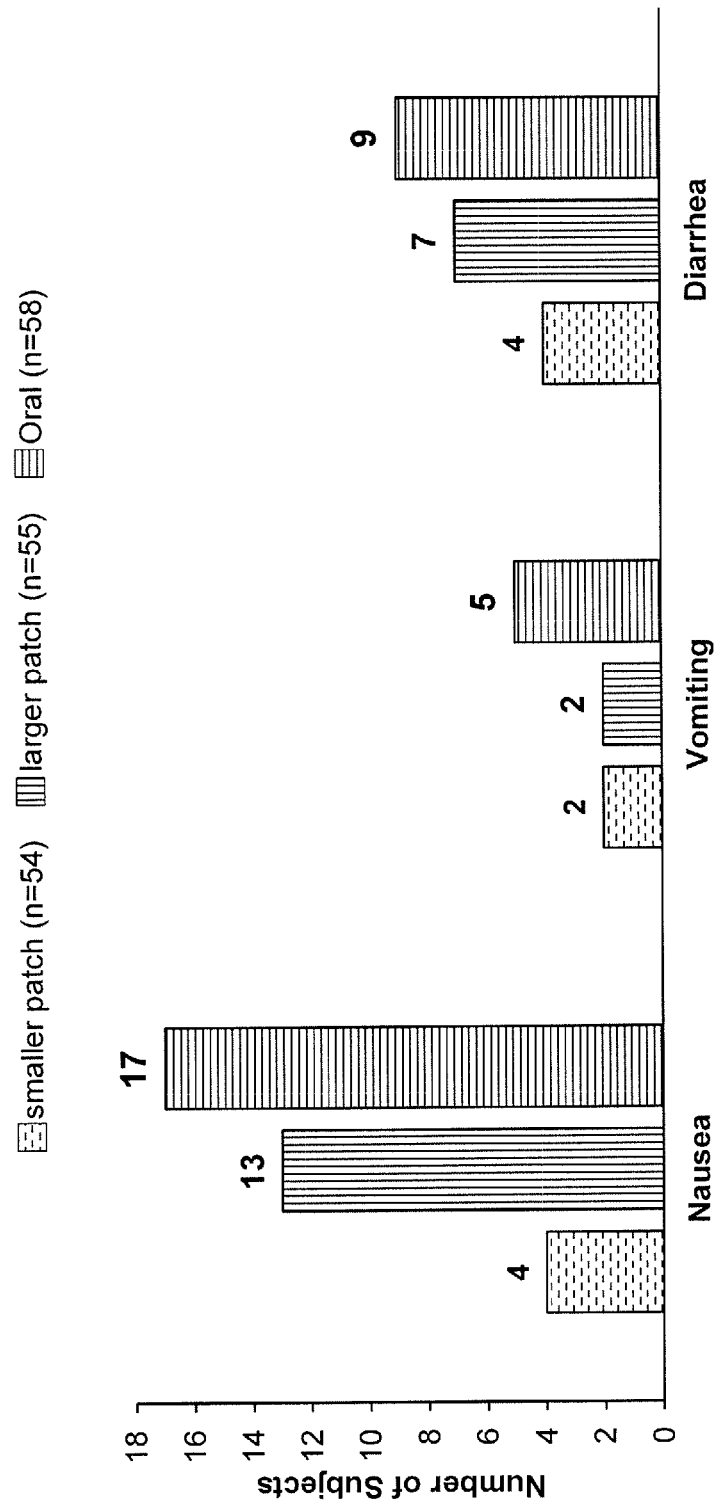
FIG. 7B is a bar graph showing the number of gastrointestinal related adverse events (nausea, vomiting and diarrhea) reported by subjects in a clinical study, where the subjects were treated as described in FIG. 7A; the bars with dashed fill correspond to subjects treated with the weekly smaller size transdermal patch, the bars with vertical line fill correspond to subjects treated with the weekly larger size transdermal patch, and the bars with horizontal line fill correspond to the subjects treated with oral donepezil.

The gastrointestinal related adverse events of nausea, vomiting and diarrhea reported by the subjects in the clinical study mentioned above with respect to FIG. 7A are shown in FIG. 7B. Subjects treated with the smaller size transdermal patch (bars with dashed fill) and with the larger size transdermal patch (bars with vertical line fill) had a lower incidence or nausea, vomiting and diarrhea than subjects treated with oral (bars with horizontal line fill) donepezil. The number of subjects experiencing nausea was four-fold lower when the 10 mg/day donepezil was administered transdermally versus orally. The number of subjects experiencing diarrhea was two-fold lower when 10 mg/day donepezil was administered transdermally versus orally. Accordingly, in one embodiment, a method for delivering donepezil to a subject is provided, where the method comprises providing a transdermal delivery system comprised of a donepezil and administering or instructing to administer the transdermal delivery system to the skin of a subject. Administering of donepezil transdermally achieves a plasma concentration of donepezil that is bioequivalent to administration of donepezil orally, and wherein the number of gastrointestinal related adverse events is two-fold, three-fold, four-fold, or five-fold lower than subjects treated with the same dose of donepezil orally. In one embodiment, the number of gastrointestinal related adverse events is between 2-5, 2-4, and 2-3 fold lover, and in another embodiment, the number of gastrointestinal related adverse events is at least about two-fold, at least about three-fold, at least about four-fold, or at least about five-fold lower than subjects treated with the same dose of donepezil orally.

III. Examples

The following examples are illustrative in nature and are in no way intended to be limiting.

Example 1

Donepezil Transdermal Delivery System

A transdermal delivery system comprising donepezil was prepared as follows.
Preparation of Drug Reservoir:
1.20 grams of sorbitan monolaurate (SPAN® 20) was dissolved in 6.00 g of triethyl citrate and mixed with 1.80 grams of lauryl lactate and 89.69 grams of ethyl acetate. 6.00 grams of glycerin (glycerol) was added and mixed. 9.00 grams of donepezil hydrochloride and 1.82 grams of sodium bicarbonate were added and dispersed in the mixture. 12.00 grams of crosslinked, micronized polyvinylpyrrolidone (KOLLIDON® CL-M) was then added and the mixture was homogenized. To the homogenized drug dispersion, 43.93 grams of acrylic acid/vinyl acetate copolymer (DURO-TAK® 387-2287, solid content 50.5%) was added and well mixed. The wet adhesive formulation was coated on a release liner and dried using a lab coater (Werner Mathis) to yield a dry coat weight of 12 mg/cm$^2$.
Preparation of Contact Adhesive:
0.60 grams of sorbitan monolaurate (SPAN® 20) was dissolved in 3.0 grams of triethyl citrate and mixed with 0.9 grams of lauryl lactate, 25.45 grams of ethyl acetate and 1.34 grams of isopropyl alcohol. 6.00 grams of crosslinked, micronized polyvinylpyrrolidone (KOLLIDON® CL-M) was added and the mixture was homogenized. To the homogenized mixture 38.61 grams of acrylic acid/vinyl acetate copolymer (DURO-TAK® 387-2287, solid content 50.5%) was added and mixed well. The wet adhesive formulation was coated on a release liner and dried to give a dry coat weight of 5 mg/cm$^2$.
Lamination and Die-Cut:
A polypropylene microporous membrane (CELGARD® 2400) was pretreated by coating it with a solvent mixture of sorbitan monolaurate, triethyl citrate and lauryl lactate to saturate the membrane with the solvent mixture. The pretreated membrane was laminated on the adhesive side of the drug reservoir. Then the contact adhesive was laminated on top of the A rate controlling membrane laminated with drug reservoir. The release liner on the drug reservoir side was replaced and laminated with backing film. The final five layer laminate was die-cut into transdermal patches.
The weight percentages of the components in the transdermal delivery system are set forth in Table 1.1 below.

TABLE 1.1

| Ingredient | wt. % in drug reservoir | wt. % in contact adhesive | total wt. % in delivery system |
|---|---|---|---|
| Donepezil HCl | 5.2% | — | 3.6% |
| Sodium bicarbonate | 1.1% | — | 0.74% |
| sorbitan monolaurate (Span ® 20) | 0.7% | 0.8% | 0.73% |
| Triethyl citrate | 3.5% | 3.9% | 3.6% |
| Lauryl lactate | 1.05% | 1.2% | 1.1% |
| Ethyl acetate | 52.3% | 33.5% | 46.6% |

TABLE 1.1-continued

| Ingredient | wt. % in drug reservoir | wt. % in contact adhesive | total wt. % in delivery system |
|---|---|---|---|
| Glycerol | 3.5% | — | 2.4% |
| crosslinked, micronized polyvinylpyrrolidone (KOLLIDON ® CL-M) | 7.0% | 7.9% | 7.3% |
| acrylic acid/vinyl acetate copolymer (DURO-TAK ® 387-2287) | 25.6% | 50.9% | 33.4% |
| isopropyl alcohol | — | 1.8% | 0.54% |

Example 2

In Vivo Administration of Donepezil from a Donepezil Transdermal Delivery System Transdermal delivery systems comprising donepezil were prepared as described in Example 1. Twelve (12) human subjects were randomized into two groups for treatment with a transdermal delivery system (n=6) or with orally administered donepezil (ARICPET®), 5 mg taken on day one and on day 7 of the study. The transdermal delivery system was applied to the skin and worn for one week and then removed. Blood samples were taken daily from the subjects treated with the transdermal delivery system. Blood samples were taken at frequent hour intervals on day 1 and day 7 in the group treated with orally delivered donepezil, and again on days 8, 10, 12 and 14. Mean plasma concentration of donepezil in the treatment groups are shown in FIGS. 2A-2B.

Example 3

Memantine Transdermal Delivery System

A transdermal delivery system comprising memantine was prepared as follows. 10 grams (g) of memantine base was dissolved in a mixture of 82.42 g ethyl acetate, 4.34 g isopropyl alcohol, 12 g of propylene glycol, and 6.48 g levulinic acid to form a clear solution. 7.0 g fumed silica (AEROSIL® 200P) was added and the mixture was homogenized. 127.8 g acrylic acid/vinyl acetate copolymer (DURO-TAK® 387-2287, solid content 50.5%) was added and mixed until the mixture become homogenous.

The adhesive formulation mixture was coated on a siliconized polyethylene terephthalate liner and dried in a Werner Mathis coater at 60° C. for 8 minutes to yield a dry adhesive layer with a coat weight of 90 gram per square meter. A transdermal delivery system was fabricated using two of the dry adhesive layers sandwiched together with a non-woven polyester fabric between the two adhesive layers. Then, coated polyethylene terephthalate liner was replaced with a backing film. Transdermal delivery systems were then die-cut from the laminate. The weight percentage of components in each adhesive layer of the system are summarized in Table 3.1

TABLE 3.1

| Ingredient | weight percent in adhesive layer and in transdermal delivery system |
|---|---|
| Memantine base | 4% |
| Ethyl acetate | 33% |
| Isopropyl alcohol | 1.7% |
| Propylene glycol | 4.8% |
| Levulinic acid | 26% |
| fumed silica (AEROSIL® 200P) | 2.8% |
| acrylic acid/vinyl acetate copolymer (DURO-TAK® 387-2287) | 51% |

Example 4

In Vivo Administration of Memantine from a Memantine Transdermal Delivery System Transdermal delivery systems comprising memantine were prepared as described in Example 3. Nineteen (19) human subjects were randomized into four groups for treatment with one of the following: (1) a memantine transdermal delivery system (n=5) worn for one week; (2) a memantine transdermal delivery system (n=7) worn for three days; (3) orally administered memantine (NAMENDA XR®), 28 mg taken on day one and on day 7 of the study. The transdermal delivery systems were applied to the skin and worn for one week (Group 1) or for 3 days (Group 2) and then removed. Blood samples were taken daily from the subjects treated with a transdermal delivery system. Blood samples were taken at frequent hour intervals on day 1 and day 7 in the group treated with orally delivered donepezil, and again on days 8, 10, 12 and 14. Mean plasma concentrations of memantine in the treatment groups are shown in FIGS. 5A-5B.

Example 5

Donepezil Transdermal Delivery Systems

Transdermal delivery system comprising donepezil was prepared as follows.

Preparation of Drug Reservoir:

Sorbitan monolaurate (SPAN® 20) was dissolved in triethyl citrate and mixed with lauryl lactate. Glycerol was added and mixed. Donepezil hydrochloride and sodium bicarbonate were added and dispersed in the mixture. Crosslinked, micronized polyvinylpyrrolidone (KOLLIDON® CL-M) was then added and the mixture was homogenized. To the homogenized drug dispersion, acrylic acid/vinyl acetate copolymer (DURO-TAK® 387-2287, solid content 50.5%) was added and well mixed. The wet adhesive formulation was coated on a release liner and dried using a lab coater (Werner Mathis).

Preparation of Contact Adhesive:

Sorbitan monolaurate (SPAN® 20) was dissolved in triethyl citrate and mixed with lauryl lactate. Crosslinked, micronized polyvinylpyrrolidone (KOLLIDON® CL-M) was added and the mixture was homogenized. To the homogenized mixture acrylic acid/vinyl acetate copolymer (DURO-TAK® 387-2287, solid content 50.5%) was added and mixed well. The wet adhesive formulation was coated on a release liner and dried.

Lamination and Die-Cut:

A polypropylene microporous membrane (CELGARD® 2400) was pretreated by coating it with a solvent mixture of sorbitan monolaurate, triethyl citrate and lauryl lactate to saturate the membrane with the solvent mixture. The pretreated membrane was laminated on the adhesive side of the drug reservoir. Then the contact adhesive was laminated on top of the rate controlling membrane laminated with drug reservoir. The release liner on the drug reservoir side was replaced and laminated with backing film. The final five layer laminate was die-cut into transdermal patches.

The weight percentage of the components in the transdermal delivery systems are set forth in Table 5.1 below.

TABLE 5.1

| Ingredient | Drug Reservoir (Dry Formula % wt/wt) | Contact Adhesive (Dry formula, % wt/wt) |
|---|---|---|
| Donepezil HCl | 16.0 | 0 |
| Sodium bicarbonate | 2.6 | 0 |
| Triethyl citrate | 10.0 | 10.0 |
| Lauryl Lactate | 3.0 | 3.0 |
| Sorbitan monolaurate (SPAN® 20) | 2.0 | 2.0 |
| Glycerol | 10.0 | 0 |
| crosslinked polyvinylpyrrolidone (KOLLIDON® CL-M) | 15.0 | 20.0 |
| acrylic acid/vinyl acetate copolymer (DURO-TAK® 387-2287) | 41.4 | 65.0 |

Example 6

Donepezil Transdermal Delivery Systems

Transdermal delivery system comprising donepezil was prepared as follows.

Preparation of Drug Reservoir:

Sorbitan monolaurate (SPAN® 20) was dissolved in triethyl citrate and mixed with lauryl lactate. Glyceol was added and mixed. Donepezil hydrochloride was added and dispersed in the mixture. Fumed silica (AEROSIL® 200 Pharma) was then added and the mixture was homogenized. To the homogenized drug dispersion, acrylic acid/vinyl acetate copolymer (DURO-TAK® 387-2287, solid content 50.5%) and dimethylaminoethyl methacrylate, butyl methacrylate, methyl methacrylate copolymer (EUDRAGIT® EPO) were added and well mixed. The wet adhesive formulation was coated on a release liner and dried using a lab coater (Werner Mathis).

Preparation of Contact Adhesive:

Sorbitan monolaurate (SPAN® 20) was dissolved in triethyl citrate and mixed with lauryl lactate. Crosslinked, micronized polyvinylpyrrolidone (KOLLIDON® CL-M) was added and the mixture was homogenized. To the homogenized mixture acrylic acid/vinyl acetate copolymer (DURO-TAK® 387-2287, solid content 50.5%) added and mixed well. The wet adhesive formulation was coated on a release liner and dried.

Lamination and Die-Cut:

A polypropylene microporous membrane (CELGARD® 2400) was pretreated by coating it with a solvent mixture of sorbitan monolaurate, triethyl citrate and lauryl lactate to saturate the membrane with the solvent mixture. The pretreated membrane was laminated on the adhesive side of the drug reservoir. Then the contact adhesive was laminated on top of the rate controlling membrane laminated with drug reservoir. The release liner on the drug reservoir side was replaced and laminated with backing film. The final five layer laminate was die-cut into transdermal patches.

The weight percentage of the components in the transdermal delivery systems are set forth in Table 6.1 below.

TABLE 6.1

| Ingredient | Drug Reservoir (Dry Formula % wt/wt) | Contact Adhesive (Dry formula, % wt/wt) |
|---|---|---|
| Donepezil HCl | 25.0 | 0 |
| dimethylaminoethyl methacrylate, butyl methacrylate, methyl methacrylate copolymer (EUDRAGIT ® EPO) | 17.7 | 0 |
| Triethyl citrate | 10.0 | 10.0 |
| Lauryl Lactate | 6.0 | 6.0 |
| Sorbitan monolaurate (SPAN ® 20) | 2.0 | 2.0 |
| fumed silica (AEROSIL ® 200 Pharma) | 7.0 | 0 |
| Glycerol | 10.0 | 0 |
| crosslinked polyvinylpyrrolidone (KOLLIDON ® CL-M) | 0 | 20.0 |
| acrylic acid/vinyl acetate copolymer (DURO-TAK ® 387-2287) | 24.3 | 64.0 |

Example 7

Memantine Transdermal Delivery System

Preparation of Drug Reservoir:

An amount of 2.0 g of glycerol and 2.0 g of octyldodecanol were mixed with a mixture of 29.35 g of ethyl acetate and 1.86 g of isopropyl alcohol. In the solution, 5.0 g of memantine hydrochloride and 1.95 g of sodium bicarbonate were dispersed by stirring. To the dispersion, 3.0 g of cross-linked polyvinylpyrrolidone (KOLLIDON® CL-M) was added and homogenized. To the homogenized dispersion, 11.99 g of acrylate copolymer (DURO-TAK® 387-2287, solid content 50.5%) was added and mixed well. The wet adhesive formulation was coated on a release liner and dried using a Werner Mathis coater to get a dry coat weight of 15 mg/cm$^2$.

Preparation of Contact Adhesive:

An amount of 2.0 g of octyldodecanol was mixed with 20.67 g of n-heptane. After addition of 4.00 g of cross-linked polyvinylpyrrolidone (KOLLIDON® CL-M) to the solution, the mixture was homogenized. To the homogenized mixture, an amount of 23.33 g of polyisobutylene/polybutylene (60/40) adhesive solution (solid content 60%) was added and mixed well. The polyisobutylene adhesive solution was a mixture of 10% polyisobutylene known as Oppanol® B-100, 50% polyisobutylene known as Oppanol® B-12 and 40% polybutene known as Indopol® H 1900. The wet adhesive formulation was coated on a release liner and dried to give a dry coat weight of 5 mg/cm$^2$.

A polypropylene microporous membrane (CELGARD® 2400) was pretreated by coating it with octyldodecanol to saturate the membrane with the solvent. The pretreated membrane was laminated between the drug reservoir layer and the contact adhesive layer. The release liner on the drug reservoir layer was replaced and laminated with a backing (3M SCOTCHPAK® 1012). The final five layer laminate was die-cut into patches.

In vitro skin flux studies were performed using a Franz type diffusion cell with an active diffusion area of 0.64 cm$^2$. Human epidermal skim was mounted between the donor and receptor compartments of the diffusion cell. The transdermal delivery system was placed over the skin and the two compartments were clamped tight together. The receptor compartment was filled with 0.01 M phosphate buffer, pH=6.5, containing 0.01% gentamicin. The solution in the receptor compartment was continually stirred using a magnetic stirring bar in the receptor compartment. The temperature was maintained at 32±0.5° C. Samples were drawn from the receptor solution at periodic intervals and the receptor solution was replaced with fresh phosphate buffers solution. Drug content in the samples was analyzed using LCMS for memantine. The flux profile (not shown) remains relatively constant over 7 days.

The weight percent of the components in each layer of the transdermal delivery systems are summarized in Tables 7.1 and 7.2 below.

TABLE 7.1

Transdermal delivery systems (with two contact adhesive formulations)

| COMPONENTS | Drug Reservoir Dry Composition (%) | Contact Adhesive #1 Dry Composition (%) | Contact Adhesive #2 Dry Composition (%) |
|---|---|---|---|
| Memantine HCl | 25% | 0 | 0 |
| Sodium bicarbonate | 9.73% | 0 | 0 |
| Octyldodecanol | 10% | 10% | 10% |
| Glycerol | 10% | 0 | 0 |
| fumed silica (AEROSIL ® 200) | 0 | 0 | 7% |
| crosslinked polyvinylpyrrolidone (KOLLIDON ® CL-M) | 15% | 20% | 0 |
| acrylic acid/vinyl acetate copolymer (DURO-TAK ® 387/87-2287) | 30.3% | 0 | 0 |
| polyisobutylene mixture | 0 | 70% | 83% |
| Total | 100% | 100% | 100% |

TABLE 7.2

Transdermal delivery system II

| | Drug Reservoir Dry Composition (%) | Contact Adhesive Dry Composition (%) |
|---|---|---|
| Memantine HCl | 25% | 0 |
| Sodium bicarbonate | 9.7% | 0 |
| Octyldodecanol | 7% | 10% |
| Glycerol | 10% | 0 |
| crosslinked polyvinylpyrrolidone (KOLLIDON ® CL-M) | 15% | 20% |
| acrylic acid/vinyl acetate copolymer (DURO-TAK ® 387/87-2287) | 33.3% | 0 |
| polyisobutylene mixture | 0 | 70% |
| Total | 100% | 100% |

Example 8

Method of Evaluating a Transdermal System

Transdermal delivery systems are prepared according to Example 6.

Approximately 60 patients are enrolled and are randomly separated into two treatment arms of 30 patients each for a four week treatment study. The patients in Arm 1 are treated with a transdermal system, where a transdermal system for delivery of 5 mg donepezil per day is worn for 7 days. After the initial 7 day period, the system is replaced weekly for 3 weeks with a transdermal system for delivery of 10 mg donepezil per day. The patients in Arm 2 are treated with a daily oral dose of 5 mg donepezil (ARICEPT) for 7 days followed by a once daily 10 mg dose of donepezil (ARICEPT) for 28 days.

For the subjects in Arm 1, blood samples are taken at the following time points to determine donepezil blood concentration and pharmacokinetics: predose; day 1 post dosing at times of 0 hours, 2 hours, 6 hours and 12 hours; days 2-15 and day 22 at 0 hour; day 20 at 0, 3 6 and 12 hours; days 30-35 at 1 and 12 hours; day 36 at 0, 2, 6 and 12 hours; days 37-38, 41, 44, 47, 50 and 54 at 0 hour.

For the subjects in Arm 2, blood samples are taken at the following time points to determine donepezil blood concentration and pharmacokinetics: day 1 at 0, 1, 2, 3, 4, 6, 8 and 12 hours; day 2, 8, 15, 22 and 29 at 0 hour; day 35 at 0, 1, 2, 3, 4, 6, 8, and 12 hours; days 36, 37, 40, 43, 46, 49 and 53 at 0 hour.

The number of subjects with treatment related adverse events is assessed daily during the 36 day confinement period and for 7 visits over a 21 day wash-out period. Assessment of local skin irritation in the subjects of Arm 1 will also be assessed daily during the 36 day confinement period and for 7 visits over a 21 day wash-out period. Skin irritation is assessed using an 8 point categorical scale of no irritation; minimal erythema, barely perceptible; definite erythema readily visible; minimal edema or minimal papular response; erythema and papules; definite edema; erythema, edema and papules; vesicular eruption; strong reaction, spreading beyond application site. Topical adhesion of the subjects in Arm 1 is assessed twice daily during the 36 day confinement period according to a percent adhesion scale of ≥90% adhered (essentially no lift off skin); ≥75% to <90% adhered (some edges only lifting off skin); ≥50% to <75% adhered (less than half the transdermal system lifting off skin); <50% adhered but did not detach (not detached, but more than half the transdermal system lifting off skin without falling off); patch completely detached (transdermal system detached, completely off skin).

Example 9

Method of Evaluating a Transdermal System

Transdermal delivery systems are prepared according to the teachings of Examples 5 and 6.

Approximately 60 patients are enrolled and are randomly separated into three treatment arms of 20 patients each for a four week treatment study. The patients in Arm 1 are treated with a transdermal system of formulation A, for delivery of 5 mg donepezil per day is worn for 7 days. After the initial 7 day period, the system is replaced weekly for 3 weeks with a transdermal system of formulation A for delivery of 10 mg donepezil per day. The patients in Arm 1 are treated with a transdermal system of formulation B, for delivery of 5 mg donepezil per day is worn for 7 days. After the initial 7 day period, the system is replaced weekly for 3 weeks with a transdermal system of formulation B for delivery of 10 mg donepezil per day. The patients in Arm 3 are treated with a daily oral dose of 5 mg donepezil (ARICEPT) for 7 days followed by a once daily 10 mg dose of donepezil (ARICEPT) for 28 days.

For the subjects in Arm 1 and Arm 2, blood samples are taken at the following time points to determine donepezil blood concentration and pharmacokinetics: predose; day 1 post dosing at times of 0 hours, 2 hours, 6 hours and 12 hours; days 2-15 and day 22 at 0 hour; day 20 at 0, 3 6 and 12 hours; days 30-35 at 1 and 12 hours; day 36 at 0, 2, 6 and 12 hours; days 37-38, 41, 44, 47, 50 and 54 at 0 hour.

For the subjects in Arm 3, blood samples are taken at the following time points to determine donepezil blood concentration and pharmacokinetics: day 1 at 0, 1, 2, 3, 4, 6, 8 and 12 hours; day 2, 8, 15, 22 and 29 at 0 hour; day 35 at 0, 1, 2, 3, 4, 6, 8, and 12 hours; days 36, 37, 40, 43, 46, 49 and 53 at 0 hour.

The number of subjects with treatment related adverse events is assessed daily during the 36 day confinement period and for 7 visits over a 21 day wash-out period. Assessment of local skin irritation in the subjects of Arm 1 will also be assessed daily during the 36 day confinement period and for 7 visits over a 21 day wash-out period. Skin irritation is assessed using an 8 point categorical scale of no irritation; minimal erythema, barely perceptible; definite erythema readily visible; minimal edema or minimal papular response; erythema and papules; definite edema; erythema, edema and papules; vesicular eruption; strong reaction, spreading beyond application site. Topical adhesion of the subjects in Arm 1 is assessed twice daily during the 36 day confinement period according to a percent adhesion scale of ≥90% adhered (essentially no lift off skin); ≥75% to <90% adhered (some edges only lifting off skin); ≥50% to <75% adhered (less than half the transdermal system lifting off skin); <50% adhered but did not detach (not detached, but more than half the transdermal system lifting off skin without falling off); patch completely detached (transdermal system detached, completely off skin).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for delivering donepezil base to a subject, comprising: providing a transdermal delivery system comprising a drug reservoir comprising a donepezil salt and an alkaline salt, applying the transdermal delivery system to the skin of a subject,
   generating, after said applying, donepezil base in situ in the drug reservoir by reaction between the donepezil salt and the alkaline salt, and
   delivering the donepezil base transdermally to the subject.

2. The method of claim 1, wherein the applying comprises applying once weekly.

3. The method of claim 1, wherein the transdermal delivery system comprises an amount of the donepezil salt sufficient to deliver to the skin between 1-25 mg of donepezil base in 24 hours.

4. The method of claim 1, wherein the transdermal delivery system comprises a drug reservoir and a contact adhesive, wherein the drug reservoir, the contact adhesive, or both comprise one of (i) sorbitan monolaurate, (ii) triethyl citrate, and (iii) lauryl lactate.

5. The method claim 1, wherein the transdermal delivery system comprises a drug reservoir comprising two of (i) lauryl lactate, (ii) triethyl citrate, and (iii) glycerol.

6. The method of claim 5, wherein the drug reservoir comprises donepezil hydrochloride and sodium bicarbonate.

7. The method of claim 6, wherein the drug reservoir additionally comprises one or both of sorbitan monolaurate and lauryl lactate.

8. A method for administering donepezil base to a subject, comprising:
applying to the skin of a subject a transdermal delivery system comprising a drug reservoir comprising (i) donepezil hydrochloride, and (ii) sodium bicarbonate, and (iii) a solvent composition comprising glycerol, triethyl citrate, lauryl lactate and sorbitan monolaurate,
generating, after said applying, donepezil base in situ in the drug reservoir by reaction between the donepezil HCl and the sodium bicarbonate; and
administering transdermally the donepezil base to the subject.

9. The method of claim 8, wherein the drug reservoir of the transdermal delivery system further comprises between about 25-65 wt % acrylate co-polymer.

10. The method of claim 8, wherein the drug reservoir of the transdermal delivery system comprises donepezil base generated in situ by reaction of between about 10-30 wt % donepezil hydrochloride and between about 0.5-10 wt % sodium bicarbonate.

11. The method of claim 10, wherein the drug reservoir of the transdermal delivery system comprises between about 5-15 wt % triethyl citrate.

12. The method of claim 11, wherein the drug reservoir of the transdermal delivery system comprises between about 1-10 wt % lauryl lactate.

13. The method of claim 12, wherein the transdermal delivery system further comprises a skin contact adhesive layer that comprises triethyl citrate, lauryl lactate and sorbitan monolaurate.

14. The method of claim 11, wherein the drug reservoir of the transdermal delivery system comprises an amount of donepezil hydrochloride sufficient to deliver a dose of donepezil base between 1-25 mg every 24 hours for at least about one week.

15. The method of claim 13, wherein the drug reservoir of the transdermal delivery system comprises between about 2-20 wt % glycerol.

16. The method of claim 1, wherein the drug reservoir comprises between about 10-30 wt % donepezil salt and between about 0.5-10 wt % alkaline salt.

17. The method of claim 1, wherein the donepezil salt is donepezil hydrochloride and the alkaline salt is sodium bicarbonate.

18. The method of claim 17, wherein the drug reservoir comprises between about 10-30 wt % donepezil HCl and between about 0.5-10 wt % sodium bicarbonate.

* * * * *